US011915742B2

(12) United States Patent
Eilert et al.

(10) Patent No.: US 11,915,742 B2
(45) Date of Patent: Feb. 27, 2024

(54) WAFER-ON-WAFER FORMED MEMORY AND LOGIC FOR GENOMIC ANNOTATIONS

(71) Applicant: Micron Technology, Inc., Boise, ID (US)

(72) Inventors: Sean S. Eilert, Penryn, CA (US);
Kunal R. Parekh, Boise, ID (US);
Aliasger T. Zaidy, Seattle, WA (US);
Glen E. Hush, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 9 days.

(21) Appl. No.: 17/885,242

(22) Filed: Aug. 10, 2022

(65) Prior Publication Data

US 2023/0050961 A1    Feb. 16, 2023

Related U.S. Application Data

(60) Provisional application No. 63/231,660, filed on Aug. 10, 2021.

(51) Int. Cl.
*G06F 13/00* (2006.01)
*G11C 11/4093* (2006.01)
(Continued)

(52) U.S. Cl.
CPC ........ *G11C 11/4093* (2013.01); *G06F 3/0656* (2013.01); *G06F 13/1673* (2013.01); *G06F 13/28* (2013.01); *G11C 7/08* (2013.01); *G11C 7/1039* (2013.01); *G11C 11/4087* (2013.01); *G11C 11/4091* (2013.01); *G11C 11/4096* (2013.01); *G16B 30/00* (2019.02); *G16B 50/10* (2019.02); *H01L 21/78* (2013.01); *H01L 22/12* (2013.01); *H01L 24/08* (2013.01); *H01L 24/48* (2013.01); *H01L 24/80* (2013.01); *H01L 25/0652* (2013.01); *H01L 25/0657* (2013.01);
(Continued)

(58) Field of Classification Search
CPC ..... G11C 11/4093; G11C 7/08; G11C 7/1039; G11C 11/4087; G11C 11/4091; G11C 11/4096; G16B 50/10; G16B 30/00; G06F 13/1673; G06F 13/28; H01L 21/78; H01L 22/12; H01L 24/08; H01L 24/48; H01L 24/80; H01L 25/0652; H01L 25/0657; H01L 25/30
See application file for complete search history.

(56) References Cited

U.S. PATENT DOCUMENTS 8,922,243 B2 *   12/2014   Jayasena .......... H03K 19/17758
                                                    326/38
9,135,185 B2 *   9/2015   Loh ...................... G06F 12/1027
(Continued)

*Primary Examiner* — Cheng Yuan Tseng
(74) *Attorney, Agent, or Firm* — Brooks, Cameron & Huebsch, PLLC

(57) ABSTRACT

A wafer-on-wafer formed memory and logic device can enable high bandwidth transmission of data directly between a memory die and a logic die. A logic die that is bonded to a memory die via a wafer-on-wafer bonding process can receive signals indicative of a genetic sequence from the memory die and through a wafer-on-wafer bond. The logic die can also perform a genome annotation lotic operation to attach biological information to the genetic sequence. An annotated genetic sequence can be provided as an output.

20 Claims, 17 Drawing Sheets

(51) Int. Cl.
*G06F 13/16* (2006.01)
*G06F 3/06* (2006.01)
*G11C 11/4096* (2006.01)
*H01L 23/00* (2006.01)
*H01L 25/065* (2023.01)
*H01L 21/78* (2006.01)
*H01L 21/66* (2006.01)
*H01L 25/18* (2023.01)
*H01L 25/00* (2006.01)
*G11C 7/08* (2006.01)
*G11C 7/10* (2006.01)
*G11C 11/408* (2006.01)
*G11C 11/4091* (2006.01)
*G16B 50/10* (2019.01)
*G16B 30/00* (2019.01)
*G06F 13/28* (2006.01)

(52) U.S. Cl.
CPC .............. *H01L 25/18* (2013.01); *H01L 25/50* (2013.01); *G06F 2213/28* (2013.01); *H01L 24/16* (2013.01); *H01L 2224/0801* (2013.01); *H01L 2224/08145* (2013.01); *H01L 2224/1601* (2013.01); *H01L 2224/16221* (2013.01); *H01L 2224/48091* (2013.01); *H01L 2224/48145* (2013.01); *H01L 2224/48221* (2013.01); *H01L 2224/80895* (2013.01); *H01L 2224/80896* (2013.01); *H01L 2225/06517* (2013.01); *H01L 2225/06524* (2013.01); *H01L 2225/06527* (2013.01); *H01L 2225/06541* (2013.01); *H01L 2225/06565* (2013.01); *H01L 2225/06589* (2013.01); *H01L 2924/1431* (2013.01); *H01L 2924/1436* (2013.01); *H01L 2924/14335* (2013.01)

(56) References Cited

U.S. PATENT DOCUMENTS

| | | | | |
|---|---|---|---|---|
| 9,170,948 | B2* | 10/2015 | Loh | G11C 5/025 |
| 9,201,777 | B2* | 12/2015 | Hsu | G06F 13/16 |
| 9,286,948 | B2* | 3/2016 | Loh | G06F 16/2455 |
| 9,535,831 | B2* | 1/2017 | Jayasena | G06F 3/0647 |
| 9,767,028 | B2* | 9/2017 | Cheng | G06F 15/7821 |
| 9,768,145 | B2* | 9/2017 | Yu | H01L 24/03 |
| 9,892,058 | B2* | 2/2018 | Wilkes | G06F 12/1027 |
| 10,198,349 | B2* | 2/2019 | Breternitz | G06F 15/7821 |
| 11,681,465 | B2* | 6/2023 | Alsop | G06F 3/0673 711/154 |
| 2020/0243486 | A1 | 7/2020 | Quader et al. | |
| 2021/0366577 | A1* | 11/2021 | Koller | G06N 20/00 |
| 2022/0171829 | A1* | 6/2022 | Snelgrove | G06F 9/30101 |
| 2022/0206685 | A1* | 6/2022 | Kalamatianos | G06F 3/0659 |
| 2023/0050961 | A1* | 2/2023 | Eilert | G06F 13/28 |
| 2023/0317656 | A1* | 10/2023 | Song | H01L 23/5283 257/777 |

* cited by examiner

WAFER-ON-WAFER FORMED MEMORY AND LOGIC FOR GENOMIC ANNOTATIONS

CROSS-REFERENCE TO RELATED APPLICATIONS

This application claims priority to U.S. Provisional Application 63/231,660, filed Aug. 10, 2021, which is incorporated by reference.

TECHNICAL FIELD

The present disclosure relates generally to memory, and more particularly to apparatuses and methods associated with the use of wafer-on-wafer memory and logic, such as for genomic annotations.

BACKGROUND

Memory devices are typically provided as internal, semiconductor, integrated circuits in computers or other electronic devices. There are many different types of memory including volatile and non-volatile memory. Volatile memory can require power to maintain its data and includes random-access memory (RAM), dynamic random access memory (DRAM), and synchronous dynamic random access memory (SDRAM), among others. Non-volatile memory can provide persistent data by retaining stored data when not powered and can include NAND flash memory, NOR flash memory, read only memory (ROM), Electrically Erasable Programmable ROM (EEPROM), Erasable Programmable ROM (EPROM), and resistance variable memory such as phase change random access memory (PCRAM), resistive random access memory (RRAM), and magnetoresistive random access memory (MRAM), among others.

Memory is also utilized as volatile and non-volatile data storage for a wide range of electronic applications. including, but not limited to personal computers, portable memory sticks, digital cameras, cellular telephones, portable music players such as MP3 players, movie players, and other electronic devices. Memory cells can be arranged into arrays, with the arrays being used in memory devices.

DETAILED DESCRIPTION

Figure 1:
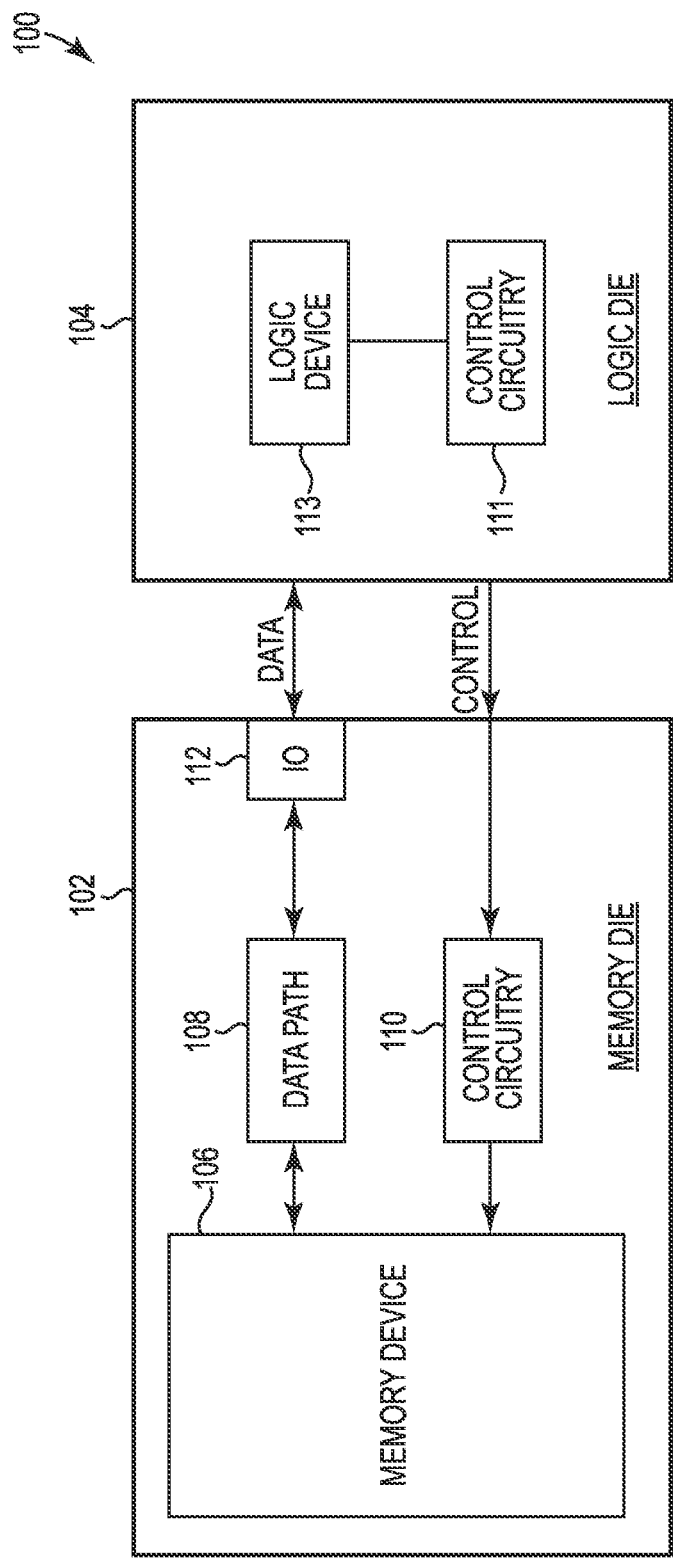
FIG. 1 is a block diagram of an apparatus in the form of a system including a memory device and a logic device.

The present disclosure includes apparatuses and methods related to wafer-on-wafer formed memory and logic and routing signals between a memory die and a logic die for performing logical operations such as annotating a genomic sequence. Logical operations (e.g., arithmetic, flow control, and combinatorial operations) can be made up of basic logical operations such as AND, OR, NOR, XOR, etc. and are generally executed on logic dies. In contrast, memory operations (e.g., load, store, etc.) are generally executed on memory dies. Inexpensive and energy-efficient logic devices have been proposed. Such devices can benefit from being tightly coupled to memory devices. Logic devices can be artificial intelligence (AI) accelerators such as deep learning accelerators (DLAs).

AI refers to the ability to improve a machine through "learning" such as by storing patterns and/or examples which can be utilized to take actions at a later time. Deep learning refers to a device's ability to learn from data provided as examples. Deep learning can be a subset of AI. Neural networks, among other types of networks, can be classified as deep learning. The low power, inexpensive design of deep learning accelerators can be implemented in internet-of-things (IOT) devices. The DLAs can process and make intelligent decisions at run-time. Memory devices including the edge DLAs can also be deployed in remote locations without cloud or offloading capability. Deep learning can be implemented utilizing multiplication operations.

A three-dimensional integrated circuit (3D IC) is a metal-oxide semiconductor (MOS) IC manufactured by stacking semiconductor wafers or dies and interconnecting them vertically using, for example, through-silicon vias (TSVs) or metal connections, to function as a single device to achieve performance improvements at reduced power and smaller footprint than conventional two-dimensional processes. Examples of 3D ICs include hybrid memory cube (HMC) and high bandwidth memory (HBM), among others.

Implementing a memory device that couples memory die and logic die using 3D IC can benefit from the efficient transfer of data between the memory die and the logic die. Transferring data from the memory die to the logic die can include transferring data from the memory die to a global data bus and transferring the data from the global data bus to the logic die. However, transferring data from the global data bus to the logic die can be inefficient.

Methods for manufacturing 3D ICs include monolithic, die-on-die, die-on-wafer, chip-on-wafer, and wafer-on-wafer. Monolithic fabrication of 3D ICs generally involves providing a first layer of circuitry and/or electronic components, depositing a semiconductor material (e.g., silicon) on the first layer, and forming a second layer of circuitry/components on the first layer and/or electronic components by processing the deposited semiconductive material. The die-on-die, die-on-wafer, and chip-on-wafer processes include dicing one or both of the wafers prior to bonding. This may require aligning and bonding individual components formed on different wafers. In contrast, the wafer-on-wafer approach forms 3D ICs by building electronic components on two separate semiconductor wafers, which are subsequently aligned, bonded, and diced to form 3D ICs. Although processes for manufacturing 3D ICs are useful, they can present various challenges. For example, those processes may require expensive and time consuming alignment and bonding operations.

Aspects of the present disclosure address the above and other deficiencies. For instance, at least one embodiment of the present disclosure can provide high bandwidth via a wide bus between a memory die and a logic die bonded via a wafer-on-wafer bonding process. While the wide bus can provide for high bandwidth between the memory die and the logic die, the memory die can also operate according to a standardized input/output interface with a host, thus providing flexibility in the use of the memory. Various embodiments can be useful for artificial intelligence accelerators, machine learning, graph analysis, databases, fluid dynamics or other memory bandwidth intensive applications, image processing, language processing, virtual or augmented reality applications, genomics, proteomics, etc.

Embodiments of the present disclosure can provide a greater bandwidth from memory within a fixed power envelope compared to some previous approaches. For example, drones typically have limited power and space available. At least one embodiment of the present disclosure can provide improved inferences based on video obtained by a drone within that constrained power and space envelope. Another example implementation is providing power and thermal relief versus multiple standard memory packages on a common circuit board (e.g., graphics double data rate 6 (GDDR6) packages). Other advantages include improving top end performance with reduced power consumption in a fairly inexpensive package (e.g., more sensors could be added to an autonomous vehicle while still operating within a given power envelope).

Genome annotation can refer to assigning a possible role, or function, to a string of nucleotides by using multiple lines of evidence to identify regions of interest. Genome annotation can consist of three main steps. The first step can be identifying portions of the genome that do not code for proteins, commonly referred to as introns. The second step can be identifying or predicting functional elements of the genome. The third step can be attaching biological information to the elements identified.

Certain aspects of genome annotation can be referred to as structural-based annotation. Structural annotation can be concerned with identifying where the regions of interest, usually genes, are in the genetic sequence or genome and what consist of. For example, structural annotation may identify where the exons and introns are located, where the untranslated regions are, the location of the open reading frames, the location of any regulatory motifs, or the overall gene structure of a particular portion of a genetic sequence. Structural annotations may be beneficial because two genes with similar structure provides a good indication that the two genes may have similar function.

Other aspects of genome annotation can be referred to as functional annotation or identifying the function of the resulting protein or peptide. Predictions of the function of the annotated genetic sequence can be made based on known functions of similar proteins or peptides. Portions of the annotated genetic sequence can be searched against known sequences with known functions.

An example implementation of one or more embodiments of the present disclosure is in a data center. Embodiments of the present disclosure can improve those efficiencies for a variety of applications. Wafer-on-wafer formed logic and memory dies can be combined in a network (e.g., a mesh network) and scaled up to perform various applications. Examples include a type-2 accelerator card, running training applications (e.g., on the fly business center data, operating on a database, etc.), among other examples. The efficiency of processes run in a data center is important for cost and energy efficiency. A compute express link (CXL) card could incorporate several wafer-on-wafer bonded logic and memory die.

An example implementation of one or more embodiments of the present disclosure is in 5G infrastructure. Smaller sized antennas with improved capabilities such as improved antenna alignment or steering, network intrusion detection, a low bandwidth link among 5G towers can be provided to enable group intelligence and state (e.g., detect multiple intrusions across towers as evidence of a concentrated attack), improved mobility through network pass off of state of inference of mobile devices between 5G towers, etc. 5G towers can be outfitted with cameras for additional municipal infrastructure awareness applications, for example. Rather than using the 5G bandwidth to transmit the camera data over a network, the camera data can be handled locally via a wafer-on-wafer bonded memory die and logic die to perform the municipal infrastructure awareness application without reducing performance of the 5G antenna. Such embodiments can also provide a lower power solution to handling the camera data versus a separate dedicated DLA to do the same. For example, a DLA can use 3 watts, memory 2 watts, and a processor 1 watt to perform analysis of the camera data. However, according to the present disclosure the wafer-on-wafer bonded memory die and logic die (e.g., DLA in this example) can operate at 3 watts and replace the separate memory and accelerator devices, saving 2 watts in this example.

An example implementation of one or more embodiments of the present disclosure is in providing privacy for speech recognition applications. Typically, according to some previous approaches, speech recognition is performed by a local sensor sending data via a network (e.g., a public network) to a server where powerful processing can occur to provide the speech recognition functionality. However, according to at least one embodiment of the present disclosure, the greater bandwidth provided between the memory die and the logic die (e.g., a speech recognition die in this example) can allow the speech recognition (or at least a portion thereof) to be performed in greater locality to the sensor, potentially avoiding exposure over networks.

The figures herein follow a numbering convention in which the first digit or digits correspond to the drawing figure number and the remaining digits identify an element or component in the drawing. Similar elements or components between different figures may be identified by the use of similar digits. For example, 202 references element "02" in FIG. 2A, and a similar element is referenced as 402 in FIG. 4B. Analogous elements within a Figure may be referenced with a hyphen and extra numeral or letter. See, for example, elements 216-1, 216-2 in FIG. 2A. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention and should not be taken in a limiting sense.

FIG. 1 is a block diagram of an apparatus in the form of a system 100 including a memory die 102 and a logic die 104. In this example, the system 100 includes a memory die 102 coupled to the logic die 104 via a wafer-on-wafer bond (not specifically illustrated in FIG. 1). The memory die 102 and logic die 104 can have various interfaces, such as input/output (IO) interface 112 (e.g., for exchanging signals indicative of data) and a control interface (e.g. for exchanging control signals). The system 100 can be part of a personal laptop computer, a desktop computer, a digital camera, a mobile telephone, a memory card reader, a server, or an Internet-of-Things (IoT) enabled device among various other types of systems.

The memory die can include a memory device 106, which can include one or more memory arrays, banks, etc. coupled to control circuitry 110 and a data path 108 of the memory die 102. The logic die 104 can include a logic device 113 and control circuitry 111 coupled thereto. The logic device 113 can be an artificial intelligence (AI) accelerator, which is also referred to herein as a deep learning accelerator (DLA) as an example. The logic device 113 can be coupled to one or more of the interfaces between the logic die 104 and the memory die 102, and thus to a data path 108 of the memory die 102. As used herein, a memory die 102, memory device 106, a logic die 104, and/or a logic device 113, for example, might also be separately considered an "apparatus.

For clarity, the system 100 has been simplified to focus on features with particular relevance to the present disclosure. The memory device 106 can be a DRAM array, SRAM array, STT RAM array, PCRAM array, TRAM array, RRAM array, NAND flash array, NOR flash array, and/or 3D cross-point array for instance. The memory device 106 may be referred to herein as a DRAM array as an example. The memory device 106 can comprise memory cells arranged in rows coupled by access lines (which may be referred to herein as word lines or select lines) and columns coupled by sense lines (which may be referred to herein as digit lines or data lines).

Although not specifically illustrated, the memory die 102 includes address circuitry to latch address signals provided over a host interface. The host interface can include, for example, a physical interface (e.g., a data bus, an address bus, and a command bus, or a combined data/address/command bus) employing a suitable protocol. Such protocol may be custom or proprietary, or the host interface may employ a standardized protocol, such as Peripheral Component Interconnect Express (PCIe), Gen-Z interconnect, cache coherent interconnect for accelerators (CCIX), or the like. The host interface can be coupled to the memory device 106 (e.g., to an array of memory cells on the memory device 106). Address signals are received and decoded by a row decoder and a column decoder to access the memory device 106. Data can be read from memory device 106 by sensing voltage and/or current changes on the sense lines using sensing circuitry. The sensing circuitry can be coupled to the memory device 106. Each memory device 106 and corresponding sensing circuitry can constitute a bank of the memory die 102. The sensing circuitry can comprise, for example, sense amplifiers that can read and latch a page (e.g., row) of data from the memory device 106. The IO circuitry 112 can be used for bi-directional data communication with the logic die 104 along a data path 108. Read/write circuitry is used to write data to the memory device 106 or read data from the memory device 106. The read/write circuitry can include various drivers, latch circuitry, etc.

Control circuitry 110 can decode signals provided by the host. The signals can be commands provided by the host. These signals can include chip enable signals, write enable signals, and address latch signals that are used to control operations performed on the memory device 106, including data read operations, data write operations, and data erase operations. In various embodiments, the control circuitry 110 is responsible for executing instructions from the host. The control circuitry 110 can comprise a state machine, a sequencer, and/or some other type of control circuitry, which may be implemented in the form of hardware, firmware, or software, or any combination of the three. In some examples, the host can be a controller external to the memory die 102. For example, the host can be a memory controller which is coupled to a processing resource of a computing device. Data can be provided to the logic die 104 and/or from the logic die 104 via data lines coupling the logic die 104 to the IO circuitry 112.

The logic device 104 can include its own control circuitry 111. The control circuitry 111 can control the logic device 104. The logic device 113 can be controlled by the control circuitry 111. In some embodiments, the logic device 113 can also be controlled by the control circuitry 110 of the memory device 102. For example, the control circuitry 110 can provide signaling to the row decoder and the column decoder to cause the transferring of data from the memory array 102 to the logic device 113 to provide an input to the logic die 104 and/or an artificial neural network (ANN) which is hosted by the logic device 113. The control circuitry 110 and/or the control circuitry 111 can cause the output of the logic die 104 and/or the logic device 113 to be provided to the IO circuitry 112 and/or be stored back to the memory device 106.

The logic device 113 can implement an ANN model, which can be trained by the control circuitry 111 and/or by an external host (not specifically illustrated). For example, the host and/or the control circuitry 111 can train an ANN model which can be provided to the logic device 113. The logic device 113 can implement the trained ANN model as directed by the control circuitry 111. The ANN can be trained to perform a desired function. In various instances, the control circuitry 111 can also control the performance of operations on the logic device 113. For example, the control circuitry 111 can direct the execution of genomic annotation operations and logical operations. The genomic annotation operations and logical operations can be used, for example, by a DLA including an ANN among other implementations of a DLA.

According to some previous approaches, after fabrication of memory die 102 on a first wafer and the logic die 104 on a second wafer, the first wafer and the second wafer can be diced (e.g., by a rotating saw blade cutting along streets of the first wafer and the second wafer) to form the respective dies 102, 104. However, according to at least one embodiment of the present disclosure, after fabrication of the dies 102, 104 on the first wafer and the second wafer, and prior to dicing, the first wafer and the second wafer can be bonded together by a wafer-on-wafer bonding process. Subsequent to the wafer-on-wafer bonding process, the dies 102, 104 can be singulated. As used herein, "singulate" refers to separating conjoined units into individual units. For example, a memory wafer can be bonded to a logic wafer in a face-to-face orientation meaning that their respective wafers (substrates) are both distal to the bond while the memory dies and logic dies are proximal to the bond. This enables individual memory die and logic die to be singulated together as a single package after the memory wafer and the logic wafer are bonded together.

Figure 2A:
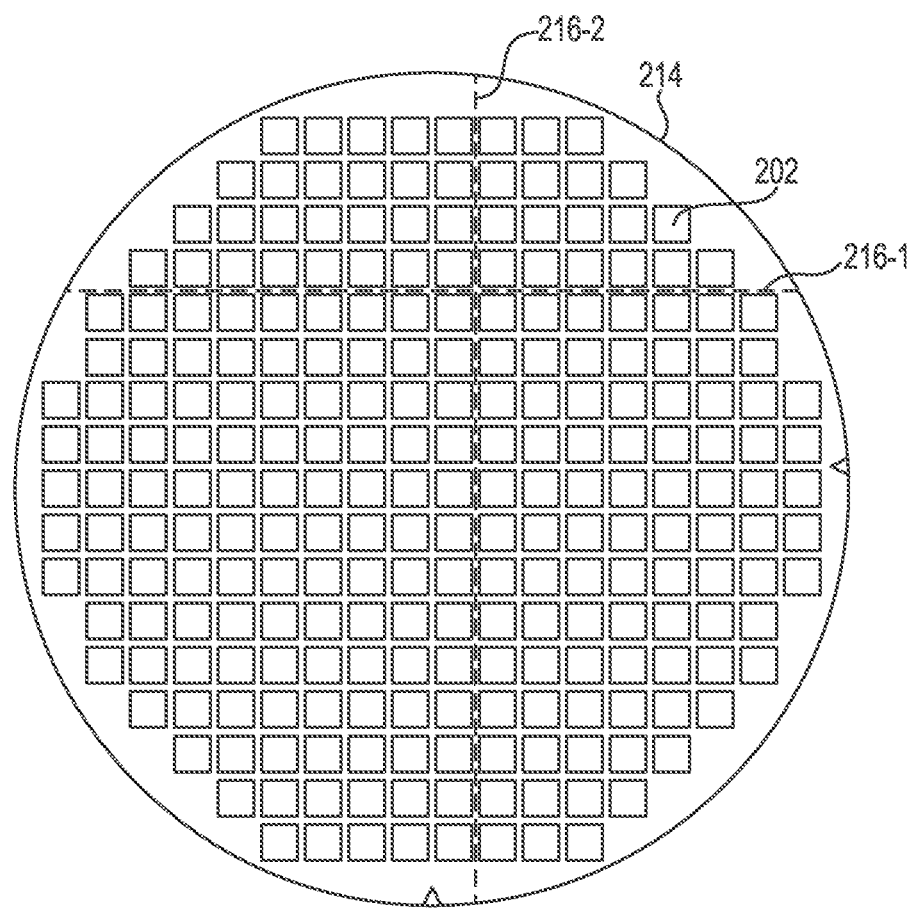
FIG. 2A is a top view of a memory wafer in accordance with a number of embodiments of the present disclosure.
Figure 2B:
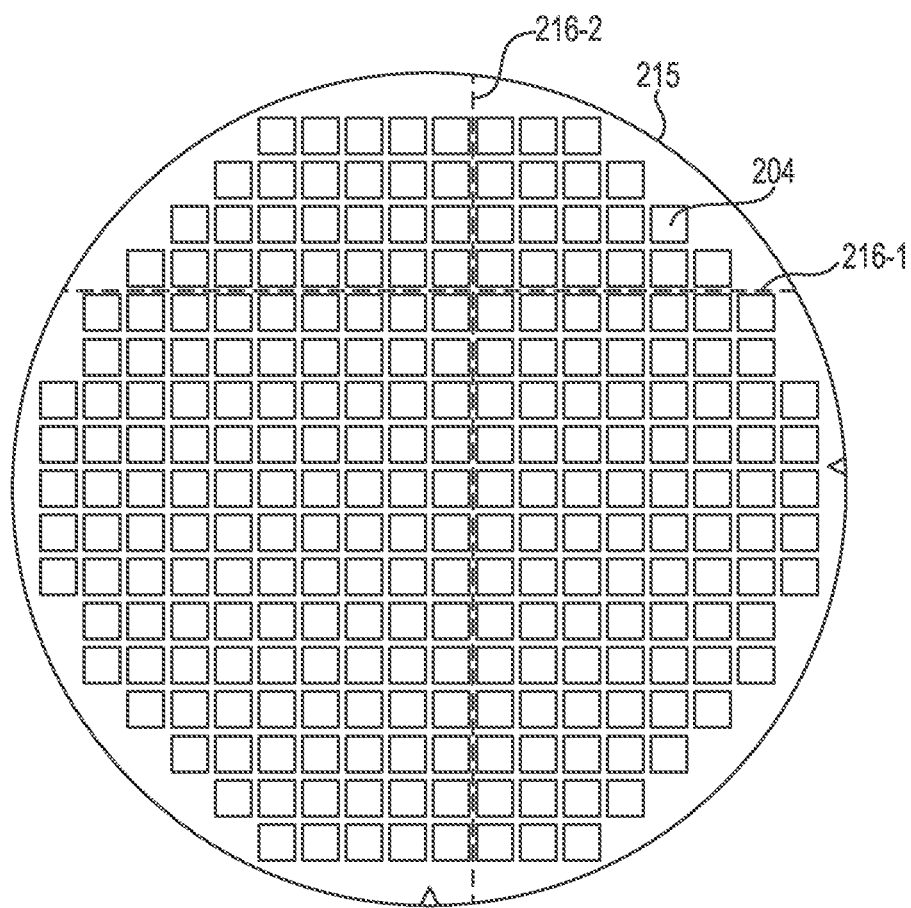
FIG. 2B is a top view of a logic wafer in accordance with a number of embodiments of the present disclosure.

FIG. 2A is a top view of a memory wafer in accordance with a number of embodiments of the present disclosure. FIG. 2B is a top view of a logic wafer in accordance with a number of embodiments of the present disclosure. As used in this disclosure, the term "wafer" can include, but is not limited to, silicon-on-insulator (SOI) or silicon-on-sapphire (SOS) technology, doped and undoped semiconductors, epitaxial layers of silicon supported by a base semiconductor foundation, and other semiconductor structures. Furthermore, when reference is made to a "wafer" or "substrate" in the following description, previous process steps may have been utilized to form regions or junctions in the base semiconductor structure or foundation.

As illustrated in FIGS. 2A-2B, the wafers 214, 215 can have a round peripheral edge. The wafers 214, 215 can include a number of dies (e.g., the memory die 202 illustrated in FIG. 2A or the logic device die 204 illustrated in FIG. 2B) having streets 216 (e.g., streets 216-1, 216-2) located therebetween. As used herein, streets 216 may be referred to as saw streets or scribe streets. The streets 216 can be paths along which a tool may cut in order to singulate the dies. Prior to a cutting, the streets 216 may be etched to a particular depth to help guide a saw blade. Furthermore, one or more side marks along the edge of the top of the wafers 214, 215 can be used to align the saw blade before cutting. In many cases, and as shown in FIGS. 2A-2B, the dies can be formed on the wafers 214, 215 such that the streets 216 are formed in perpendicular rows and columns.

The dies can comprise electronic devices. In some embodiments, each die on a particular wafer can be a same type of device. For example, each die on the wafer 214 illustrated in FIG. 2A can be a memory die 202 and each die on the wafer 215 illustrated in FIG. 2B can be a logic device 204. As used herein, an electronic device can include transistors, capacitors, diodes, memory devices, processors, other devices, and/or integrated circuits. Examples of the logic device 204 include application specific integrated circuits (ASICs) such as a DLA, a radio frequency communication circuit, a gene sequencing circuit, a gene annotation circuit, a video or imaging circuit, an audio circuit, a sensor circuit, a radar circuit, packet routing circuit, intrusion-detection circuit, safety monitoring circuit, cryptographic circuit, blockchain circuit, smart sensor circuit, 5G communication circuit, etc.

Each memory die can include an array of memory cells configured on a die or chip and local input/output (LIO) lines for communication of data on the die or chip. Further, each memory die can include transceivers associated with (e.g., coupled to) the LIO lines. The transceivers can be configured to selectively enable communication of the data to one or more devices off the die or chip. Further, each memory die can include memory-to-logic circuitry coupled to the transceivers and configured to be coupled to a logic die via a wafer-on-wafer bond. In some embodiments, more than one of the memory dies share memory-to-logic circuitry. In some embodiments, at least one memory-to-logic circuitry is configured to be coupled to logic dies via the wafer-on-wafer bond.

Testing infrastructure can be formed in association with the wafers 214, 215 and/or the dies 202, 204. Embodiments of the present disclosure can be implemented without changing the fabrication and/or use of the testing infrastructure. If testing of an individual die 202, 204 indicated that the die was bad, according to some previous approaches, the die 202, 204 would not be used in an electronic device. However, according to at least one embodiment of the present disclosure, the die 202, 204 can be abandoned in place so that the remainder of the wafer 214, 215 can be used. The counterpart die 202, 204 corresponding to the bad memory die 202, 204 can be disabled.

In some previous approaches, after fabrication of the electronic devices on the wafers 214, 215, the wafers 214, 215 can be diced (e.g., by a rotating saw blade cutting along the streets 216). However, according to at least one embodiment of the present disclosure, after fabrication of the devices on the wafers 214, 215, and prior to dicing, the wafers 214, 215 can be bonded together by a wafer-on-wafer bonding process. Subsequent to the wafer-on-wafer bonding process, the dies can be singulated. The memory wafer 214 can be bonded to the logic wafer 215 in a face-to-face orientation meaning that their respective substrates (wafers) are both distal to the bond while the memory dies and logic dies are proximal to the bond.

In some embodiments, the size of the devices on the first wafer 214 is the same as the size of the devices on the second wafer 215. The streets 216 on the first wafer 214 can be in a same relative position as the streets 216 on the second wafer 215. This enables individual memory die 202 and logic die 204 to be singulated together as a single package after the wafers 214, 215 are bonded together.

Although not specifically illustrated, in some embodiments, the size of the devices on the first wafer 214 and the second wafer 215 are proportionally different. For example, a logic die 204 on the second wafer 215 can have the same footprint as four memory die 202 on the first wafer 214. When the wafers 214, 215 are bonded together, the four memory die 202 and one logic die 204 can be singulated as a single package. As another example, the memory die 202 on the first wafer 214 can have the same footprint as four logic dies 204 on the second wafer 215. When the wafers 214, 215 are bonded together, the four logic die 204 and one memory die 202 can be singulated as a single package, which may be referred to as a network-on-wafer package. Embodiments are not limited to a 4:1 ratio of die sizes.

Embodiments including differently sized memory dies 202 and logic dies 204 may further benefit from the testing described above. For example, for logic dies 204 that are smaller than memory dies 202, the dies 202, 204 can be tested and the wafers 214, 215 can be rotated before bonding such that a greatest possible number of known good logic dies 204 are bonded to known good memory dies 202. Analogously, for memory dies 202 that are smaller than logic dies 204, the dies 202, 204 can be tested and the wafers 214, 215 can be rotated before bonding such that a greatest possible number of known good memory dies 202 are bonded to known good logic dies 204. Different memory wafers 214 and logic wafers 215 can be mixed and matched to provide a greatest combination of known good memory dies 202 and logic dies 204, regardless of whether the dies 202, 204 are differently sized.

Whichever wafer 214, 215 includes the smaller devices will have some streets 216 that are not intended to be cut. Additional connections (e.g., metal layers) can be formed across these streets 216 since they will not be cut. The additional connections across streets 216 can be used to connect multiple individual memory die 202 or logic die 204 to each other prior to the wafer-on-wafer bonding process. Such embodiments can thus create wafer level networks of memory die 202 or logic die 204. In at least one embodiment, the first wafer 214 can include multiple networked memory die 202 forming a wafer-scale memory device. The networks can be peer-to-peer networks, for example.

Figure 2C:
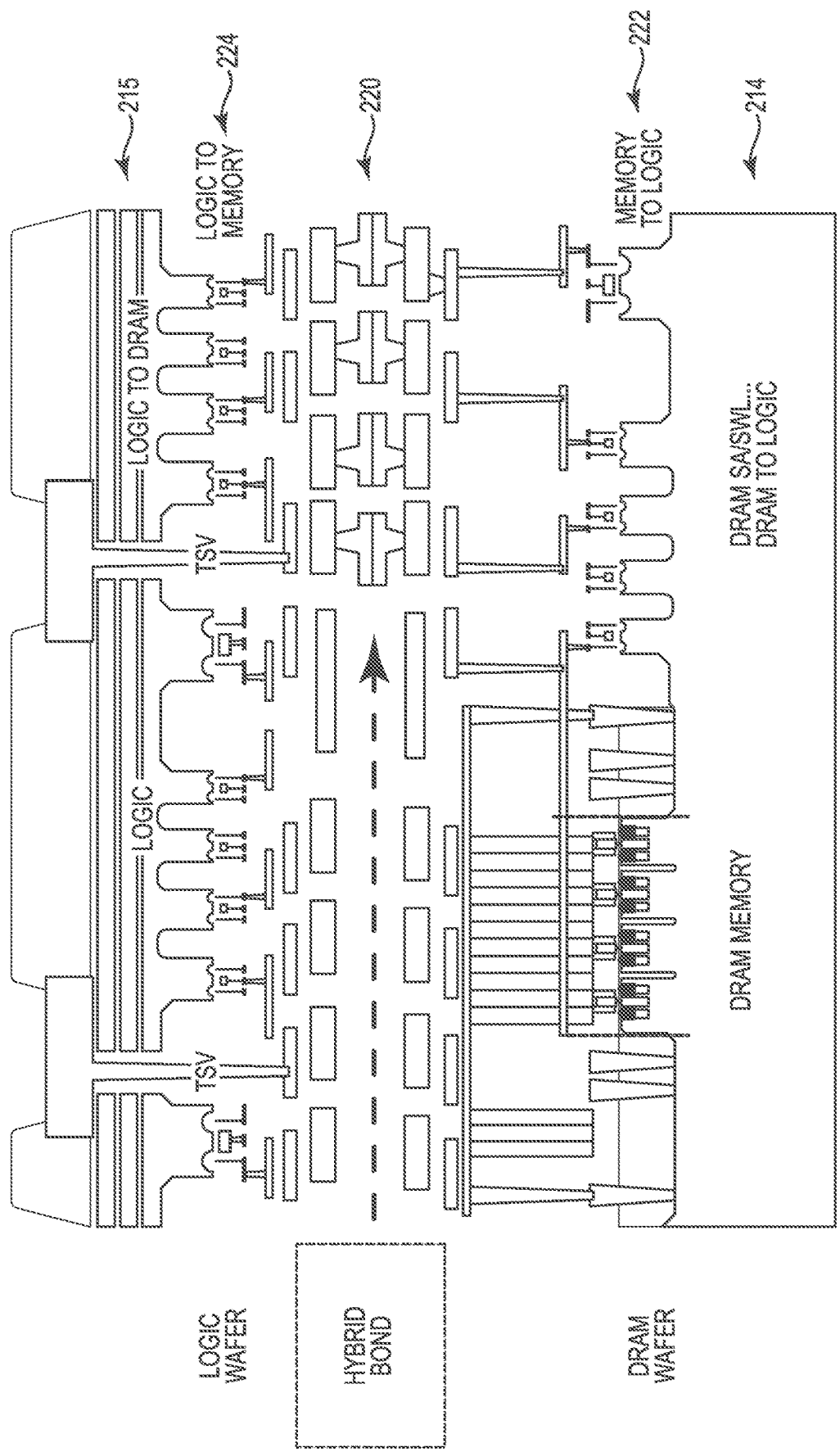
FIG. 2C is a cross-section of a portion of the memory wafer bonded to the logic wafer in accordance with a number of embodiments of the present disclosure.

FIG. 2C is a cross-section of a portion of the memory wafer 214 bonded to the logic wafer 215 in accordance with a number of embodiments of the present disclosure. The memory wafer 214 can include multiple memory dies formed thereon. Each memory die can have a memory device formed thereon. The memory device can include an array of memory cells. The memory wafer 214 includes memory-to-logic circuitry 222 formed thereon. In some embodiments, each memory die has discrete memory-to-logic circuitry 222 formed thereon. The memory-to-logic circuitry 222 can be coupled to the array of memory cells. The memory-to-logic circuitry 222 is configured to provide an electrical connection for the transfer of data and/or control signals between at least one memory die of the memory wafer 214 and at least one logic die of the logic wafer 215. In at least one embodiment, the memory-to-logic circuitry can include as few as two additional metal layers beyond what is typically included for a DRAM memory die.

The logic wafer 215 can include multiple logic dies formed thereon. Each logic die can include a logic device formed thereon. The logic device can include logic circuitry configured to perform logical operations on data. The logic wafer 215 can include logic-to-memory circuitry 224 formed thereon. In some embodiments, each logic die has discrete logic-to-memory circuitry 224 formed thereon. The logic-to-memory circuitry 224 can be coupled to the logic circuitry. The logic-to-memory circuitry 224 is configured to provide an electrical connection for the transfer of data and/or control signals between at least one logic die of the logic wafer 215 and at least one memory die of the memory wafer 214. A bond 220 is formed between the memory-to-logic circuitry 222 of the memory wafer 214 and the logic-to-memory circuitry 224 of the logic wafer 215 in the wafer-on-wafer bonding process. The bond 220 may be referred to as a hybrid bond or a wafer-on-wafer bond herein. The bond 220 can include one or more of a metal bond and direct dielectric-dielectric bond. The bond 220 enables the transmission of electrical signals between the logic-to-memory circuitry 224 and the memory-to-logic circuitry 222.

The memory-to-logic circuitry 222 can be configured to transmit signals indicative of data between the array of memory cells and the logic-to-memory circuitry 224 via the bond 220. The logic-to-memory circuitry 224 can be configured to transmit signals indicative of data between the logic circuitry and the memory-to-logic circuitry 222 via the bond 220.

The memory-to-logic circuitry 222 of the memory wafer 214 and/or the bond 220 can include bond pads at the transceiver, which can be associated with an LIO prefetch bus and/or sense amplifier (sense amp) stripe. In one example, one sense amp stripe includes 188 LIO connection pairs covering 9 array cores and 9216 pairs per channel. In another example, one sense amp stripe includes 288 LIO connection pairs and 4608 pairs per channel. Embodiments are not limited to these specific examples. The transceivers are described in more detail herein. The interconnect load of the bond 220 can be less than 1.0 femtofarads and 0.5 ohms. In one example implementation, the maximum number of rows of memory capable of being activated at one time (e.g., 32 rows) can be activated and transmit signals indicative of data via the bond 220 to the corresponding logic dies of the logic wafer 215. The memory-to-logic circuitry 222 and/or the bond 220 can include at least one power and at least one ground connection per transceiver (e.g., sense amp stripe). In at least one embodiment, the power connection is such that it allows activation of multiple rows of memory at once. In one example, the wafer-on-wafer bonding provides 256 k data connections at a 1.2 micrometer pitch.

In some embodiments, the bond 220 can include analog circuitry (e.g., jumpers) without transistors in the path between the memory die 202 and the logic die 204. One die 202, 204 can drive a signal therebetween and the other die 202, 204 can sink the signal therebetween (e.g., rather than passing signals between the dies 202, 204 via logic gates). In at least one embodiment, the bond 220 can be formed by a low temperature (e.g., room temperature) bonding process. In some embodiments, the bond 220 can be further processed with an annealing step (e.g., at 300 degrees Celsius).

Although not specifically illustrated, in at least one embodiment a redistribution layer can be formed between the memory wafer 214 and the logic wafer 215. The redistribution layer can enable compatibility of a single memory design to multiple ASIC designs. The redistribution layer can enable memory technologies to scale without necessarily scaling down the logic design at the same rate as the memory technology (e.g., circuitry on the memory die 202 can be formed at a different resolution than the circuitry on the logic die 204 without having to adjust the bond 220 and/or other circuitry between the memory die 202 and the logic die 204).

Figure 2D:
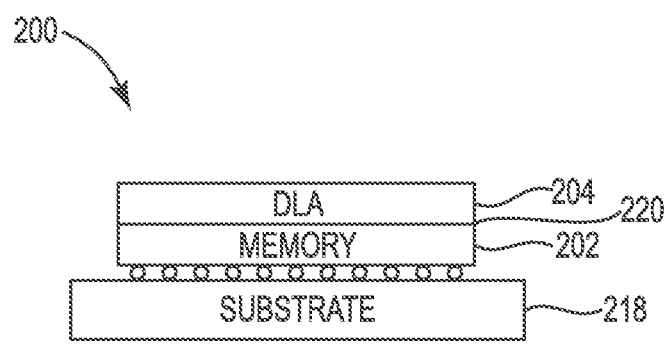
FIG. 2D illustrates a portion of the bonded wafers including a memory die and a logic die after dicing in accordance with a number of embodiments of the present disclosure.

FIG. 2D illustrates a portion of the bonded wafers including a memory die 202 and a logic die 204 after dicing in accordance with a number of embodiments of the present disclosure. The memory die 202 is illustrated as being bonded to a substrate 218, however, in at least one embodiment, the logic die 204 can be bonded to the substrate 218 instead of the memory die 202. The substrate 218, memory die 202, bond 220, and logic die 204 can form a system 220, such as an integrated circuit, configured to perform one or more desired functions. Although not specifically illustrated, the substrate 218 can include additional circuitry to operate, control, and/or communicate with the memory die 202, logic die 204, and or other off-chip devices.

According to at least one embodiment of the present disclosure, the typical functionality of the memory die 202 does not change for typical memory operations. However, data can alternatively be transferred from the memory die 202 to the logic die 204 directly via the bond 220 instead of being routed through the typical input/output circuitry of the memory die 202. For example, a test mode and/or refresh cycle of the memory die 202 can be used to transfer data to and from the logic die 204 via the bond 220 (e.g., via LIOs of the memory die 202). Using the refresh cycle for an example existing DRAM memory device, with 8 rows per bank active and a refresh cycle time of 80 nanoseconds (versus 60 nanoseconds for a single row) with 4 banks in parallel and 16 nanosecond bank sequencing, the bandwidth would be 443 gigabytes/second. However, according to at least one embodiment of the present disclosure, with the wafer-on-wafer bond 220, with 32 rows per bank active, the refresh cycle time can approach 60 nanoseconds for 32 banks in parallel and without bank sequencing, the bandwidth is 5 terabytes/second using 8 watts. Such a significant bandwidth of data being sent from the memory device would overwhelm a typical interface and/or host device. However, certain logic devices (such as a DLA) can be configured to make use of that data bandwidth via the connections provided by the bond 220. Reduced off-chip movement of data can help reduce the power consumption associated with operating the memory in this fashion.

Although not specifically illustrated, multiple memory die 202 can be stacked on one another via a bond analogous to the bond 220. Such additional memory die 202 can include memory-to-memory circuitry analogous to the memory-to-logic circuitry 222 illustrated in FIG. 2C. Alternatively, or additionally, TSVs can be used for communication of data between or through stacked memory die 202. The bond pads between stacked memory die 202 can be at locations that are replicated on stacked memory die 202 in a vertical orientation (as illustrated) such that the stacked memory die 202 are in alignment. The stacked memory die 202 can be formed by a conventional process or by wafer-on-wafer bonding (between different memory wafers) in different embodiments.

Although not specifically illustrated, the die that is bonded to the substrate 218 (e.g., the memory die 202 (as illustrated) or the logic die 204) can have TSVs formed therein to enable communication with circuitry external to the memory die 202 and logic die 204. The TSVs can also be used to provide power and ground contacts. Compared to the contacts provided by wafer-on-wafer bonding, TSVs generally have greater capacitance and a larger pitch and do not have as great of a bandwidth.

Although not specifically illustrated, in some embodiments an additional component can be bonded to the system 200. For example, a thermal solution component can be bonded to the top of the logic die 204 to provide cooling for the system 200. The physically close connection between the logic die 204 and the memory die 202 may generate heat. The thermal solution can help dissipate heat for the system 200.

Although not specifically illustrated, in some embodiments an additional component (non-volatile memory) can be bonded to the system 200 (e.g., in order to persistently store a model for the ANN). However, in some embodiments, the non-volatile memory is not necessary because the models may be relatively small and frequently updated.

Figure 3A:
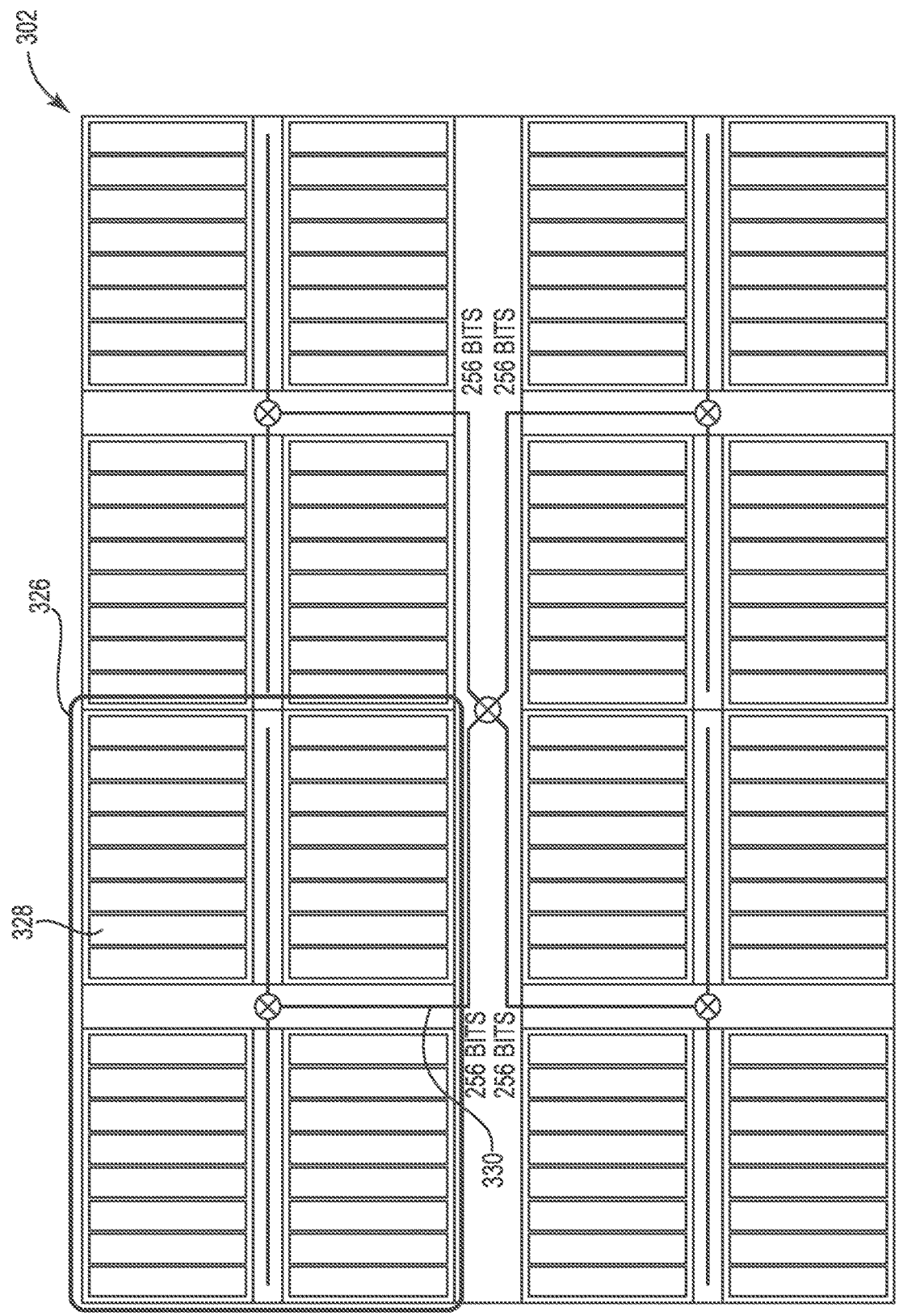
FIG. 3A illustrates a circuit diagram of a memory die in accordance with a number of embodiments of the present disclosure.

FIG. 3A illustrates a circuit diagram of a memory die 302 in accordance with a number of embodiments of the present disclosure. The example memory die 302 includes 16 memory banks 328 arranged in bank groups 326 of 4 banks. Each bank group 326 is coupled to a global data bus 330 (e.g., a 256 bit wide bus). Embodiments are not limited to these specific examples. The global data bus 330 can be modeled as a charging/discharging capacitor. The global data bus 330 can conform to a memory standard for sending data from the memory die 302 via an IO bus. However, although not specifically illustrated in FIG. 3A, according to at least one embodiment of the present disclosure, the memory die 302 can include additional transceivers for communicating data with a logic die via a wafer-on-wafer bond.

Figure 3B:
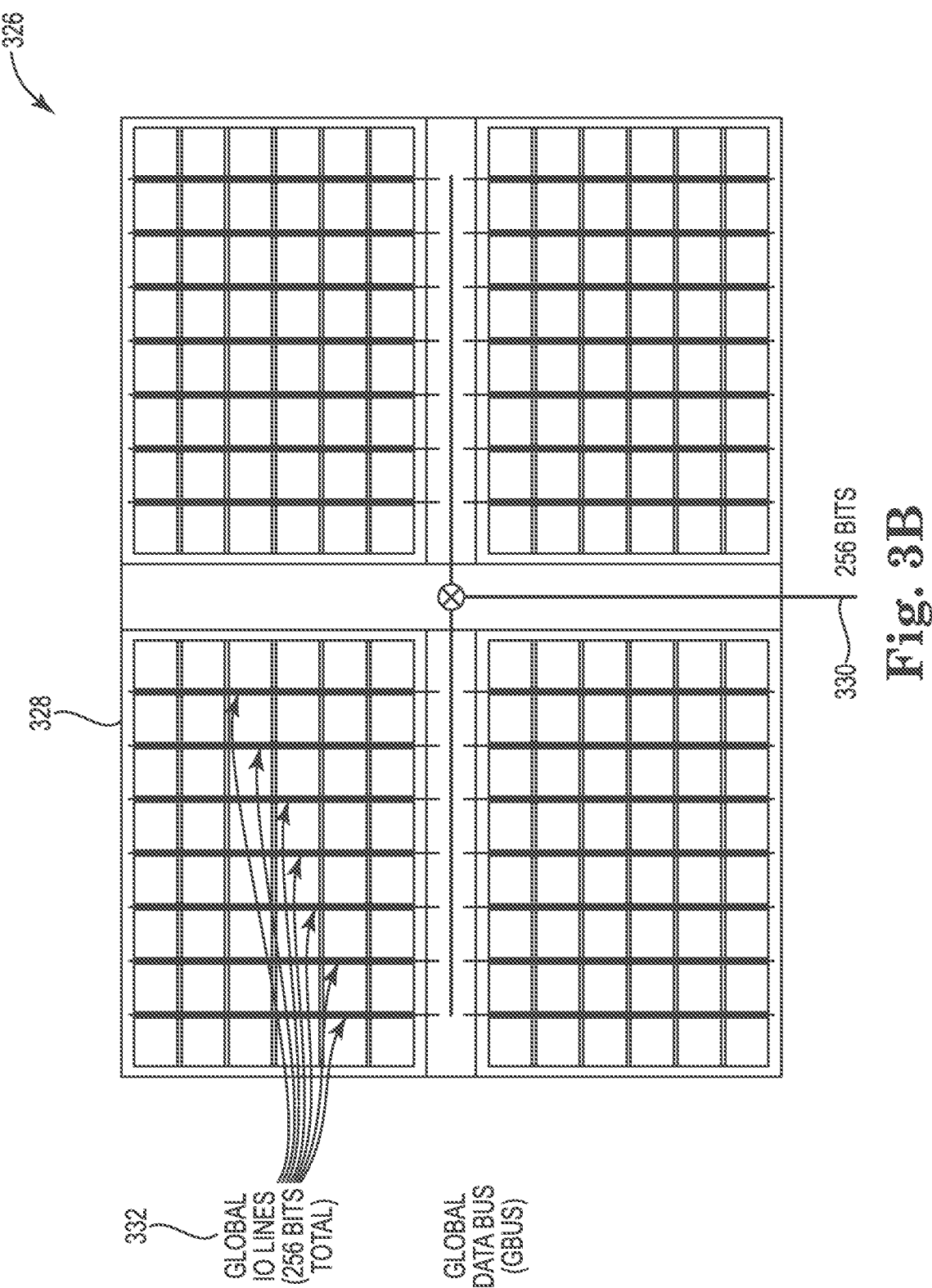
FIG. 3B illustrates a circuit diagram of a memory bank group in accordance with a number of embodiments of the present disclosure.

FIG. 3B illustrates a circuit diagram of a memory bank group 326 in accordance with a number of embodiments of the present disclosure. The memory bank group 326 can include 4 memory banks 328 as illustrated, or another quantity of banks. Each memory bank 328 can include respective global input/output (IO) lines 332 that ultimately connect to the global IO bus 330. In this example, the bank group 326 is capable of transmitting 256 bits at one time.

Figure 3C:
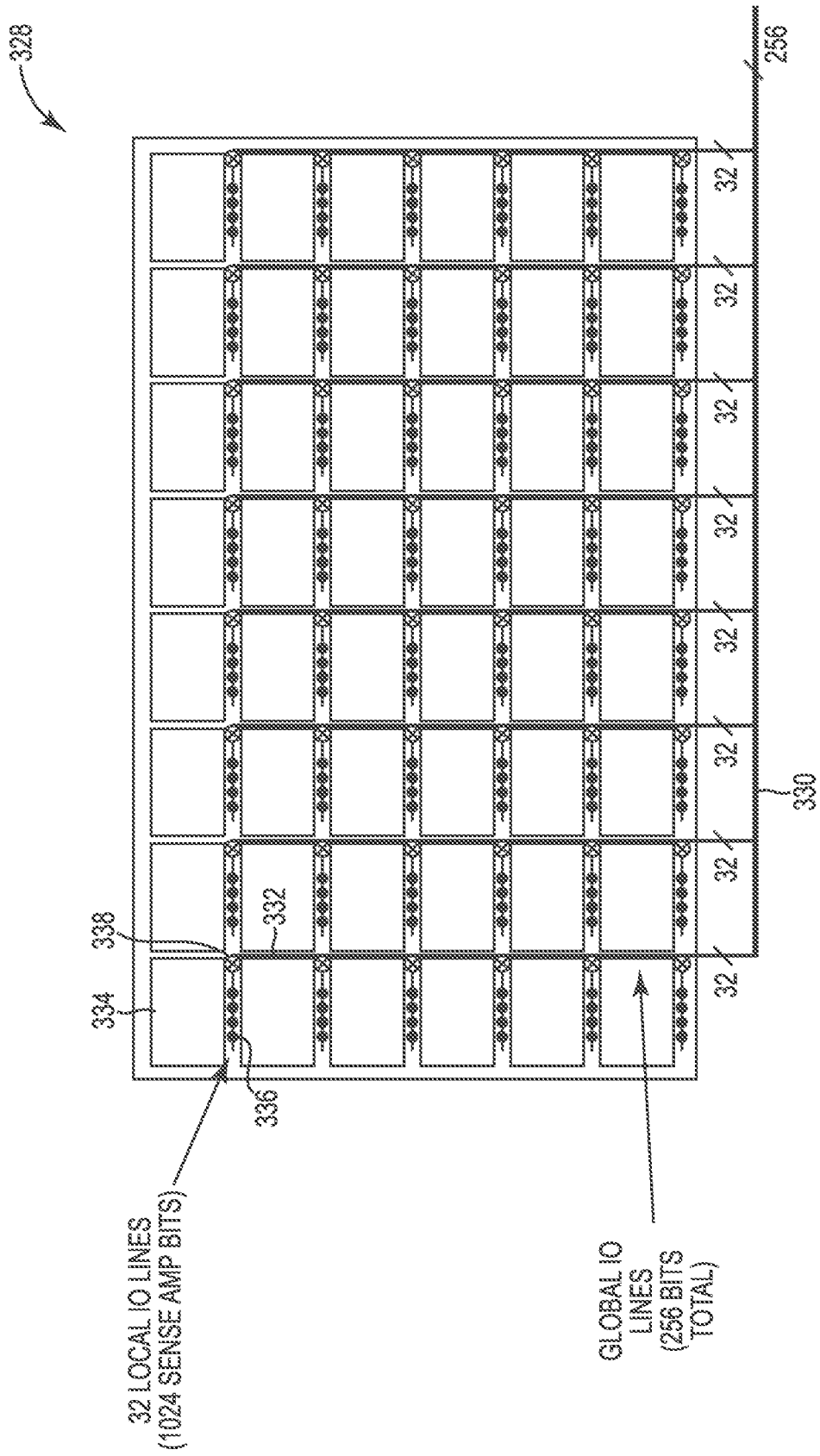
FIG. 3C illustrates a memory bank in accordance with a number of embodiments of the present disclosure.

FIG. 3C illustrates a memory bank 328 in accordance with a number of embodiments of the present disclosure. The memory bank 328 includes a quantity of memory tiles 334, each including a respective quantity of LIO lines 336 on the die or chip represented by the filled dots. Although only four filled dots are illustrated, the four filled dots can represent any number of LIO lines (e.g., 32 LIO lines). Each tile 334 can include a respective array of memory cells configured on the die or chip coupled to sense lines and access lines of the die or chip. The array of memory cells can include a quantity of rows and a quantity of columns of memory cells (e.g., 1024×1024). For example, each tile can include 32 LIOs 336. In some embodiments, each LIO line 336 can be coupled to a respective global IO line 332 (e.g., 32 LIOs can be coupled to 32 global IO lines). Each subset of sense lines is coupled to a respective IO line, and the LIOs 336 in each tile are coupled to a respective global IO line 332. In some embodiments, each global IO line 332 is coupled to respective transceivers (e.g., transceiver 338 as illustrated in FIG. 3C). For example, there can be a respective transceiver 338 associated with each tile 334 and coupled to a corresponding global IO line 332. In some embodiments, each LIO line 336 can have an independent transceiver or circuitry connected to a transceiver that multiplexes a quantity of LIO lines 336. Such an embodiment is illustrated in FIG. 3D.

Tiles can be coupled to the global I/O line (e.g., I/O bus). LIOs 336 can be coupled to a global I/O line 332 for communication of data on the die or chip via the global I/O bus 330. Each transceiver can be selectively enabled to transmit data off-chip (e.g., to a logic die via a wafer-on-wafer bond) instead of to the corresponding global IO line 332. As used herein, communication of data on the die or chip means that signals indicative of data are transmitted within a memory die or memory chip. As used herein, communication of data to one or more devices off the die or chip means that signals indicative of data are transmitted between a memory die or memory chip and a logic die or logic chip. Multiple sense amplifiers can be multiplexed into a single transceiver 338. Each transceiver 338 can be coupled to a respective contact with a corresponding logic die via a wafer-on-wafer bond. The wafer-on-wafer bond provides pitch control sufficiently fine to allow for such contacts, which would otherwise not be possible.

In at least one embodiment, the transceiver 338 can receive an enable/disable command from the corresponding logic die coupled thereto (e.g., as opposed to receiving the command from a host). In some embodiments, the enable/disable command can be received by multiple transceivers 338 (e.g., the enable/disable command can cause signals indicative of data from a particular row in each bank 328 to be transferred via the corresponding transceivers 338). The control and operation of the multiple transceivers 338 is similar to having thousands of memory controllers, except that they transfer data rather than controlling all operations. Such operation can be beneficial, for example, for applications that involve massively parallel memory access operations. For an example memory device that is configured to include an 8 kilobit row, 256 bits of data can be prefetched per transceiver 338. Therefore, each transceiver 338 can have 256 bits bonded out. In other words, at least one embodiment of the present disclosure can transfer 256 bits of data for each 8 kilobits of stored data (in this example architecture). In contrast, according to some previous approaches with an analogous architecture, a typical memory interface (e.g., via a global IO) would only be able to transfer 256 bits for 4 gigabits of stored data.

Figure 3D:
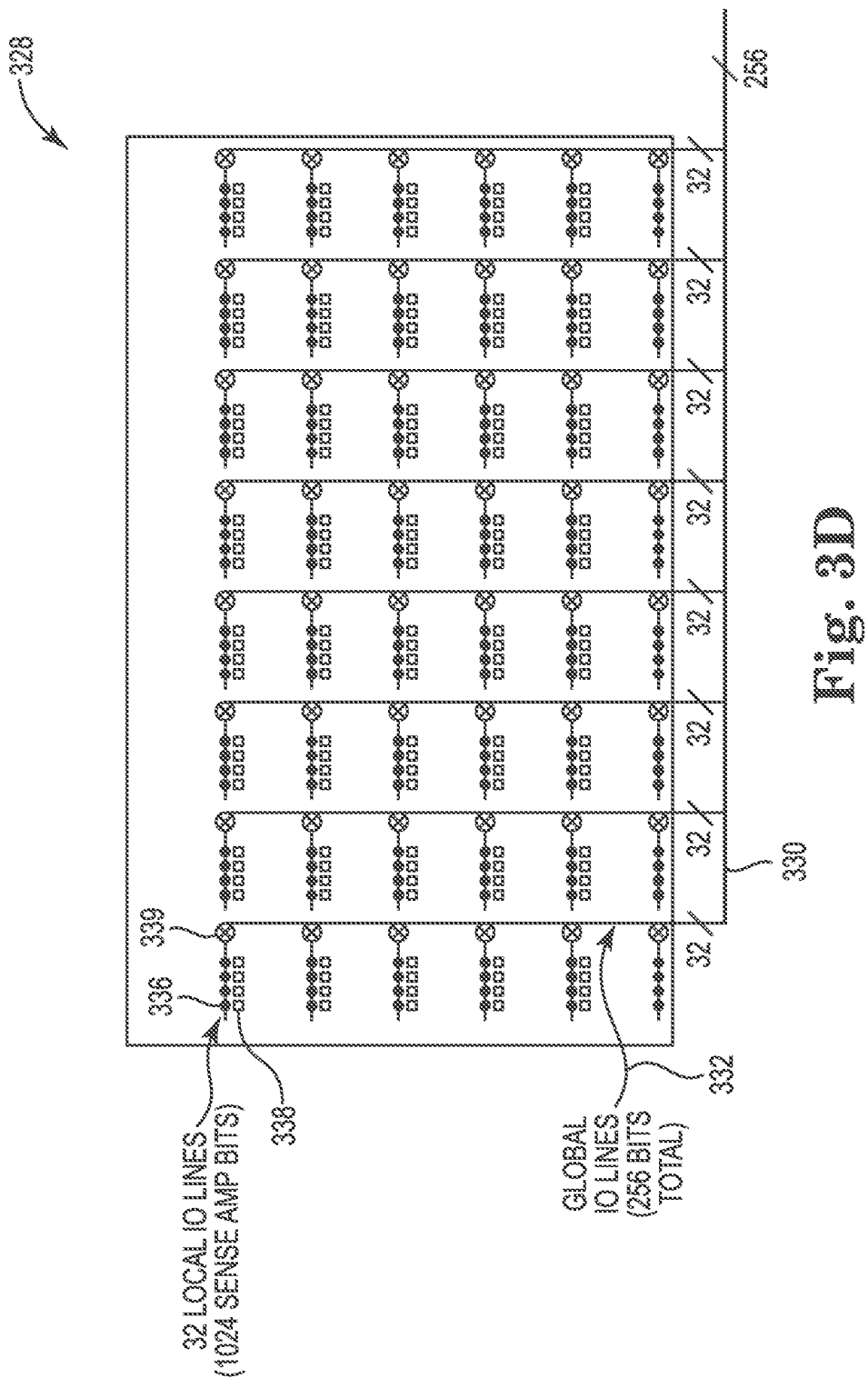
FIG. 3D illustrates a memory bank in accordance with a number of embodiments of the present disclosure.

FIG. 3D illustrates a memory bank 328 in accordance with a number of embodiments of the present disclosure. Similar to FIG. 3C, the memory bank 328 includes a quantity of memory tiles. However, the tiles are not individually drawn or enumerated in FIG. 3D. Each tile includes a respective quantity of LIO lines 336 represented by the filled dots. The LIOs 336 are coupled to a respective global IO line 332 via a multiplexer 339. Further, a respective transceiver 338 is coupled to each of the LIO lines 336, such that signals indicative of data can be transferred between the memory die and the logic die with a finer granularity versus the embodiment illustrated in FIG. 3C.

Each respective transceiver 338 is coupled to a respective LIO line 336 and thereby to a global IO line 332 and the memory-to-logic circuitry (e.g., the memory-to-logic circuitry 222 illustrated in FIG. 2C). The transceiver 338 is configured to provide a first electrical connection between a corresponding LIO line 336 and the global IO line 332 and a second electrical connection between the corresponding LIO line 336 and the memory-to-logic circuitry.

Figure 3E:
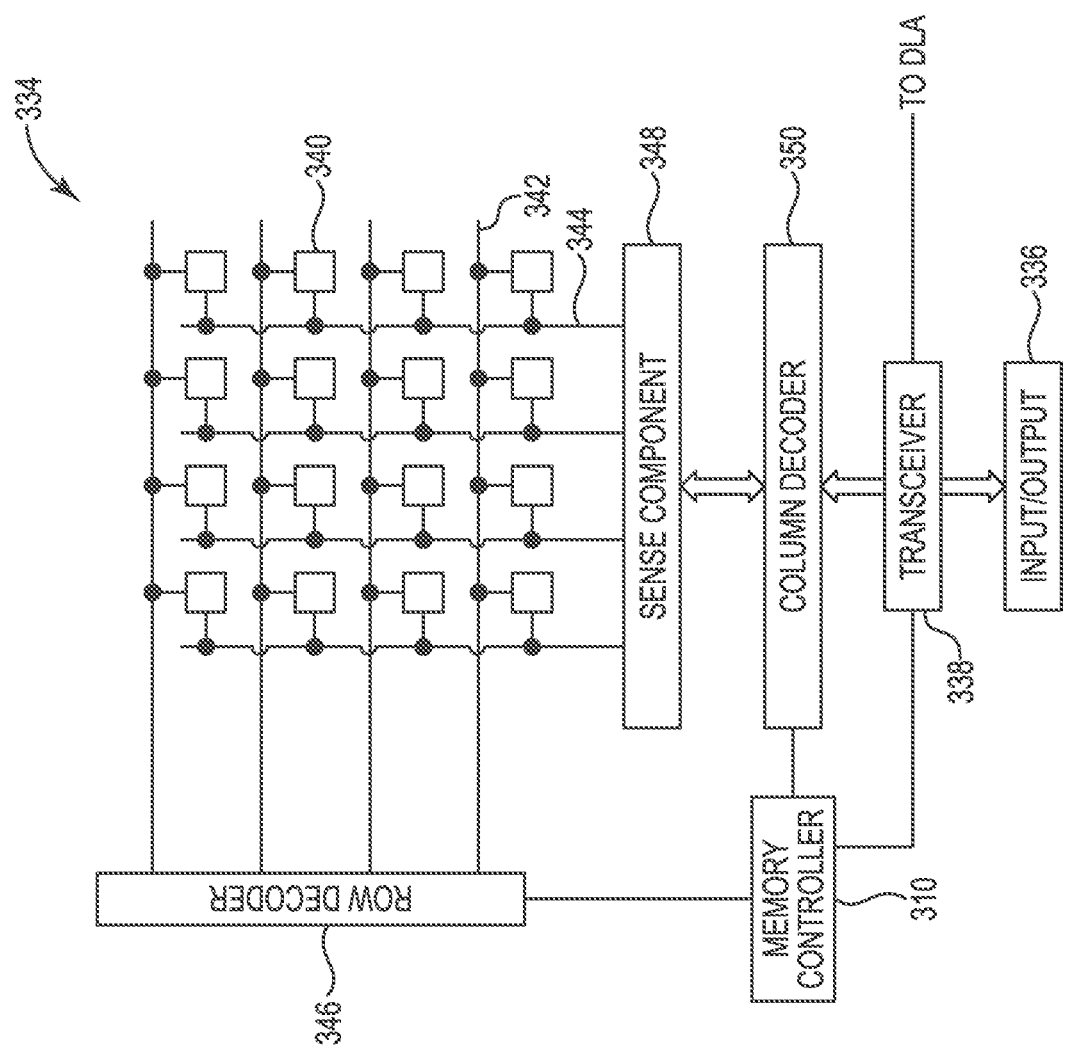
FIG. 3E illustrates a memory tile in accordance with a number of embodiments of the present disclosure.

FIG. 3E illustrates a memory tile 334 in accordance with a number of embodiments of the present disclosure. The memory tile 334 includes memory cells 340 that are programmable to store different states. Each memory cell 340 may be programmable to store two states, denoted as a logic 0 and a logic 1. In some cases, a memory cell 340 is configured to store more than two logic states. A memory cell 340 may include a capacitor to store a charge representative of the programmable states; for example, a charged and uncharged capacitor may represent two logic states. DRAM architectures may commonly use such a design, and the capacitor employed may include a dielectric material with linear electric polarization properties.

Operations such as reading and writing may be performed on memory cells 340 by activating or selecting the appropriate access line 342 and sense line 344. Activating or selecting an access line 342 or a sense line 344 may include applying a voltage potential to the respective line. Access lines 342 and sense lines 344 may be made of conductive materials. In some examples, access lines 342 and sense lines 344 are made of metals (e.g., copper, aluminum, gold, tungsten, etc.). Each row of memory cells 340 are connected to a single access line 342, and each column of memory cells 340 are connected to a single sense line 344. The intersection of an access line 342 and a sense line 344 may be referred to as an address of a memory cell 340.

In some architectures, the storage component of a cell 340 (e.g., a capacitor) may be electrically isolated from the digit line by a selection device. The access line 342 may be connected to and may control the selection device. For example, the selection device may be a transistor and the access line 342 may be connected to the gate of the transistor. Activating the access line 342 results in an electrical connection between the capacitor of a memory cell 340 and its corresponding sense line 344. The sense line 344 may then be accessed to either read or write the memory cell 340.

Accessing memory cells 340 may be controlled through a row decoder 346 and a column decoder 350. For example, a row decoder 346 may receive a row address from the memory controller 310 and activate the appropriate access line 342 based on the received row address. Similarly, a column decoder 350 receives a column address from the memory controller 310 and activates the appropriate sense lines 344. Thus, by activating an access line 342 and sense lines 344, memory cells 340 may be accessed. The column decoder 250 can be coupled to each subset of the sense lines 344 and the respective LIO line.

Upon accessing, a memory cell 340 may be read, or sensed, by sense component 348. For example, sense component 348 may compare a signal (e.g., a voltage) of the relevant sense line 344 to a reference signal (not shown) in order to determine the stored state of the memory cell 340. If sense line 344 has a higher voltage than the reference voltage, then sense component 348 may determine that the stored state in memory cell 340 was a logic 1 and vice versa. The sense component 348 can be coupled to sense lines 344 and each subset of the sense lines 344 is coupled to a respective LIO line 336 for communication of data on the die or chip.

The sense component 348 may include various transistors or amplifiers in order to detect and amplify a difference in the signals, which may be referred to as latching. In some cases, sense component 348 may include or be referred to as a sense amplifier. The sense component 348 can represent a stripe of multiple sense amplifiers. The detected logic state of memory cell 340 may then be output through column decoder 350 and to an LIO line 336. In some embodiments, a transceiver can be coupled to each respective sense amplifier and configured to retrieve data from the sense amplifier.

However, according to at least one embodiment of the present disclosure, the memory controller 310 can send a signal to the transceiver 338, to selectively route the signals indicative of data off-chip (e.g., to a logic die "to DLA") instead of to the normal IO path (e.g., via the LIO line 336). The memory controller 310 can cause the transceiver 338 to either allow signals indicative of data to either continue on the typical path (e.g., via the LIO line 336) or be sent to a wafer-on-wafer bonded logic die via the bonds and contacts described herein. The illustrated path from the transceiver 338 ("To DLA") is a representation of the electrical pathway between the memory tile 334 and the corresponding logic die (not illustrated in FIG. 3D). Embodiments of the present disclosure can preserve the functionality and fabrication of a standardized memory interface while allowing for the functionality and fabrication of an additional high bandwidth interface from the memory die to a logic die via the wafer-on-wafer bond. The transceiver 338 can extract signals indicative of data from near the sense component 348 and transfer it to the logic die. The transceiver 338 can be coupled to a host interface (e.g., via the LIO line 336). The transceiver 338 can be configured to select a data output path for the memory array between the host interface and the memory-to-logic circuitry.

In some embodiments, the transceiver 338 can be coupled between the column decoder 350 and the respective LIO line 336. Further, in some embodiments, the transceiver 338 can be embedded in the column decoder 350. Control circuitry (e.g., memory controller 310) coupled to the respective transceiver 338 can be configured to send a control signal to the transceiver 338 to selectively enable communication of the data to one or more devices off the die or chip.

Memory cells 340 may be set, or written, by activating the relevant access line 342 and sense line 344. Activating an access line 342 electrically connects the corresponding row of memory cells 340 to their respective digit lines 115. By controlling the relevant sense line 344 while the access line 342 is activated, a memory cell 340 may be written (a logic value may be stored in the memory cell 340). The column decoder 350 may accept data, for example via the LIO line 336, to be written to the memory cells 340.

However, according to at least one embodiment of the present disclosure, the transceiver 338 can be configured to enable communication of data to one or more devices off the die or chip. For example, control circuitry (e.g., the memory controller 310) can be configured to send a signal to the transceiver 338, to enable communication of the data to one or more devices off of the die or chip by selectively routing signals indicative of data to or from off-chip (e.g., from a logic die) instead of from the normal IO path (e.g., via the LIO line 336). The memory controller 310 can cause the transceiver 338 to either allow signals indicative of data to be received from the typical path (e.g., via the LIO line 336) or be received from a wafer-on-wafer bonded logic die via the bonds and contacts described herein. In some embodiments, communication of data on the die or chip can occur on a first portion of a memory device and communication of data to one or more devices off the die or chip can occur in a second portion of a memory device simultaneously. Operation of the first portion of the memory device can be independent of operation of the second portion of the memory device. In some embodiments, the memory device can be a DRAM memory device.

A memory device can include a multiplexor coupled to the sense lines 344. The memory device can also include a transceiver 338 configured to receive a control signal to switch the memory device between a first mode of operation and a second mode of operation. In the first mode of operation, the transceiver 338 can be configured to enable communication of data on the die or chip. In some embodiments, communication of data to one or more devices off the die or chip can be disabled in the first mode of operation. In the second mode of operation, the transceiver 338 can be configured to enable communication of data to one or more devices off the die or chip. In some embodiments, communication of data on the die or chip can be disabled in the second mode of operation.

The memory controller 310 can be configured to operate the transceiver 338 in a first mode to route signals indicative of data from the array off of the memory device via a global IO line (downstream of the LIO line 336). The memory controller 310 can be configured to operate the transceiver 338 in a second mode to route signals indicative of data from the array to the logic die via the memory-to-logic circuitry.

In some embodiments, signals indicative of data corresponding to the communication of data to one or more devices off the die or chip travel through the LIO lines. The LIO lines can couple memory dies to circuitry outside of the memory dies (e.g., to DLAs). Signals indicative of data can be transferred between the memory dies and circuitry outside of the memory dies through the LIO lines. In some embodiments, a bandwidth of the communication of data to one or more devices off the die or chip can be greater than a bandwidth of the communication of data on the die or chip. The bandwidth of the communication of data to one or more devices off the die or chip can be greater than the communication of data on the die or chip because the communication of data to one or more devices off the die or chip can involve more LIO lines than communication of data on the die or chip. For example, multiple LIO lines can be used to transfer data off-chip. However, one LIO line (at a time) may be used to transfer data on-chip. Further, a sense amplifier of a memory die can be directly coupled to circuitry outside of the memory die. In such embodiments, data can be transferred off-chip at the speed the data leaves the sense amplifier. However, data being transferred on-chip can travel at the speed of the bandwidth of the global IO.

In some memory architectures, accessing the memory cell 340 may degrade or destroy the stored logic state and re-write or refresh operations may be performed to return the original logic state to memory cell 340. In DRAM, for example, the capacitor may be partially or completely discharged during a sense operation, corrupting the stored logic state. Additionally, activating a single access line 342 may result in the discharge of all memory cells in the row; thus, several or all memory cells 340 in the row may need to be re-written. Some memory architectures, including DRAM, may lose their stored state over time unless they are periodically refreshed by an external power source. For example, a charged capacitor may become discharged over time through leakage currents, resulting in the loss of the stored information. Logic states may be re-written during a re-write operation or refreshed during a refresh operation.

The control circuitry (e.g., memory controller 310) may control the operation (e.g., read, write, re-write, refresh, etc.) of memory cells 340 through the various components, for example, row decoder 346, column decoder 350, and sense component 348. Memory controller 310 may generate row and column address signals in order to activate the desired access line 342 and sense line 344. Memory controller 310 may also generate and control various voltage potentials used during the operation of memory tile 334. For example, memory controller 310 may operate a selection component to isolate a sense line 344 (e.g., from a corresponding capacitor) during sensing. In general, the amplitude, shape, or duration of an applied voltage discussed herein may be adjusted or varied and may be different for the various operations for operating memory array. Furthermore, one, multiple, or all memory cells 340 within the memory tile 334 may be accessed simultaneously; for example, multiple or all cells of memory tile 334 may be accessed simultaneously during a reset operation in which all memory cells 340, or a group of memory cells 340, are set to a single logic state.

In some embodiments, an apparatus (e.g., memory device) can be configured to simultaneously access a first access line in a row of a first tile and a second access line in the same row of second tile for communication of the data. In this context, the "same row" means that the rows positionally correspond to each other (e.g., the rows line up if the tiles are positioned side-by-side). It does not necessarily mean that the rows are physically connected to each other. Further, a memory device can be configured to simultaneously access a first access line in a first row of a first tile and second access line in a second row of a second tile for communication of data. In this context, the first and second rows do not positionally correspond to each other (e.g., they do not line up if positioned side-by-side). The memory device can also be configured to access each tile synchronously or asynchronously. As used herein, asynchronously access each tile refers to accessing different tiles at different times. Asynchronously accessing the tiles can avoid large power spikes that can result from accessing a certain amount of tiles simultaneously.

Figure 3F:
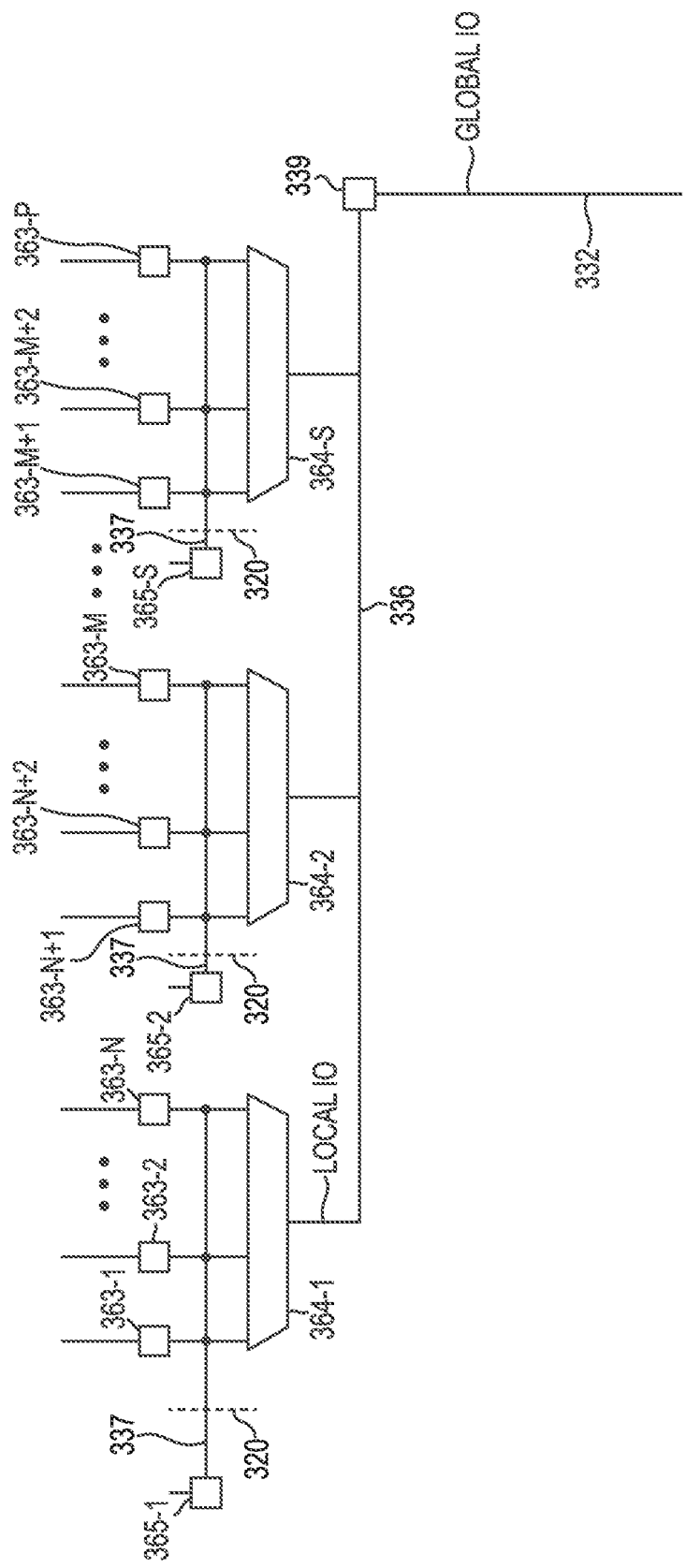
FIG. 3F illustrates a portion of a memory tile in accordance with a number of embodiments of the present disclosure.
Figure 3G:
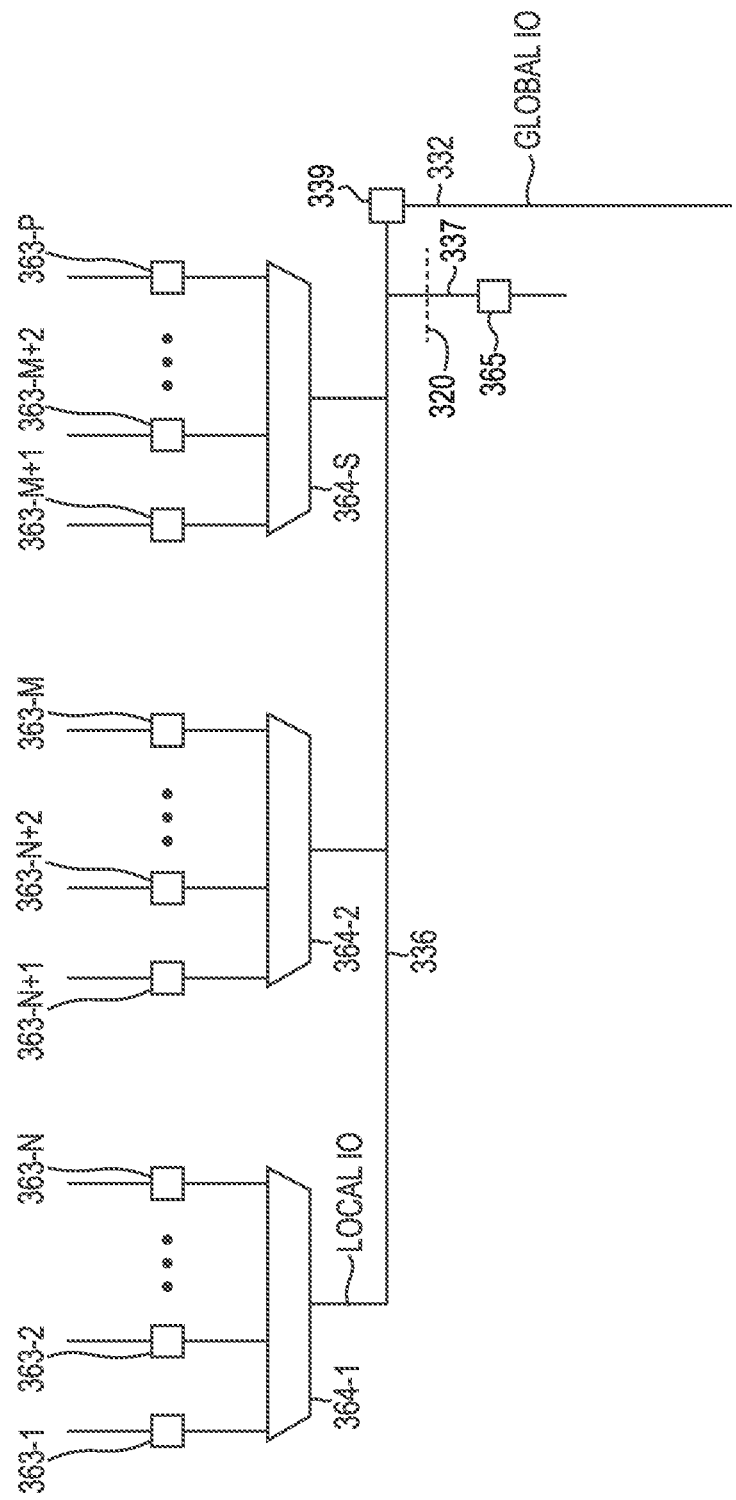
FIG. 3G illustrates a portion of a memory tile in accordance with a number of embodiments of the present disclosure.

In the embodiments of FIGS. 3C-3E, the transceivers 338 that control transfer of signals indicative of data between the memory die and the logic die are located on the logic die are located on the memory die. In the embodiments of FIGS. 3F-3G, the transceivers 365 are located on the logic die. The transceivers 365 on the logic die can be coupled to the logic-to-memory circuitry (e.g., the logic-to-memory circuitry 224 illustrated in FIG. 2) and to the logic circuitry. The transceivers 365 can be configured to select a data output path for the memory array between a host interface of the memory device and the memory-to-logic circuitry (e.g., the memory-to-logic circuitry 222 illustrated in FIG. 2).

FIG. 3F illustrates a portion of a memory tile in accordance with a number of embodiments of the present disclosure. The portion of the tile includes sense amplifiers 363-1, 363-2, . . . , 363-N, 363-N+1, 363-N+2, . . . , 363-M, 363-M+1, 363-M+2, . . . , 363-P and multiplexers 364-1, 364-2, . . . , 364-S. The portion of the tile also includes the multiplexer 339 of the memory die. For clarity, FIG. 3F has been simplified to focus on components and circuitry of a memory die and a logic die with particular relevance to the present disclosure.

The multiplexer 339 is differentiated from the transceivers 365-1, 365-2, . . . , 365-S. The multiplexer 339 can be configured to receive signals from the LIO lines 336. The multiplexer 339 selects a portion of the LIO lines 336. The multiplexer 339 can amplify the signals received from the selected portion of the LIO lines 336. The multiplexer 339 can also cause the amplified signals to be transmitted via the global IO lines 332. The multiplexer 339 can also receive signals from the global IO lines 332 and reduce the received signals. The multiplexer 339 can further transmit the reduced signals to the LIO lines 336. Although having the same name ("multiplexor"), the multiplexer 339 is different than the multiplexers 364 and has different functions than the multiplexers 364.

The transceivers 365-1, 365-2, . . . , 365-S can also receive signals, select a portion of the signals, amplify the portion of the signals, and transmit the amplified signals. However, the transceivers 365-1, 365-2, . . . , 365-S can transmit the amplified signals to the logic die and not the global IO lines 332.

The memory die can include the sense amplifiers 363, the multiplexers 364, and the multiplexer 339. The memory die can also include an LIO line 336 and a global IO line 332.

In various examples, a wafer-on-wafer bond 320 can couple the output of the sense amplifiers 333 to the transceivers 365 of the logic die. The transceivers 365 can be controlled by the logic die to cause the output of the sense amplifiers 363 to be provided to circuitry of the logic die. For example, a transceiver 365-1 can cause signals output from the sense amplifiers 363-1, 363-2, . . . , 363-N to be provided to circuitry of the logic die that is downstream from the transceiver 365-1. Although a single transceiver 365-1 is shown, the transceiver 365-1 can represent multiple transceivers such that each of the outputs of the sense amplifiers 363-1, 363-2, . . . , 363-N is provided concurrently to the circuitry downstream from the multiple transceivers of the logic die. The transceivers 365-2 can cause the output of the sense amplifiers 363-N−1, 363-N+2, . . . , 363-M to be provided to circuitry of the logic die. The transceivers 365-S can cause the output of the sense amplifiers 363-M+1, 363-M+2, . . . , 363-P to be provided to circuitry of the logic die.

Control circuitry of the logic die (e.g., the control circuitry 111 described in association with FIG. 1) can send a signal to the transceivers 365, to selectively route the signals indicative of data off-chip (e.g., to the logic die). The illustrated path from the sense amplifiers 363 to the transceivers 365 of the logic die is a representation of the electrical pathway between the memory die and the logic die. Embodiments of the present disclosure can preserve the functionality and fabrication of a standardized memory interface while allowing for the functionality and fabrication of an additional high bandwidth interface from the memory die to the logic die via the wafer-on-wafer bond 320.

In various examples, each of the transceivers 365 can be coupled to multiple sense amplifiers 363. For example, the transceiver 365-1 can be coupled to the sense amplifiers 363-1, 363-2, . . . , 363-N. The transceiver 365-2 can be coupled to the sense amplifiers 363-N+1, 363-N+2, . . . , 363-M. The transceiver 365-S can be coupled to the sense amplifiers 363-M+1, 363-M+2, . . . , 363-P. In various instances, each of the transceivers 365 can multiple signals. For example, the transceiver 365-1 can direct the signals provided from the sense amplifiers 363-1, 363-2, . . . , 363-N at a same time. The transceiver 365-2 can redirect the signals provided from the sense amplifiers 363-N+1, 363-N+2, . . . , 363-M at a same time. The transceiver 365-S can direct signals provided from the sense amplifiers 363-M+1, 363-M+2, . . . , 363-P at a same time.

Control circuitry of the logic die can cause signals indicative of data to be received at the logic die from atypical IO path including the LIOs 336 utilizing the transceiver 365. Control circuitry of the memory die (e.g., the control circuitry 116 described in association with FIG. 1) can cause signals indicative of data to be provided through a typical input/output path utilizing the LIOs 336, the multiplexer 339, and the global IO line 332. In various instances, the transceivers 365 can route signals concurrently. For example, the transceiver 365-1 can route signals between the sense amplifiers 363-1, 363-2, . . . , 363-N and the logic die concurrently with the routing of signals by the transceiver 365-2, . . . , and/or transceiver 365-S. In various examples, the transceiver 365-1 can route signals between the sense amplifiers 363-1, 363-2, . . . , 363-2 and the logic die concurrently.

Although not shown, the transceivers of the logic die coupled to multiple memory devices can route signals from the memory die to the logic die concurrently. For example, the transceivers 365 can route data with other transceivers coupled to different memory devices concurrently. Control circuitry can activate rows of multiple memory devices concurrently to cause corresponding sense amplifiers (e.g., including sense amplifiers 363) to latch signals. The transceivers (e.g., including the transceivers 365) coupled to different memory devices can route signals from the sense amplifiers of the memory devices to the logic die concurrently. The logic die can concurrently receive a greater quantity of signals from the memory die via the transceivers 365 than would be possible to output via the global IO lines 332 or a global bus. Similarly, the logic die can provide a greater quantity of signals concurrently to the memory die via the transceivers 365 than would be possible via the global IO lines 332 or a global bus. The transceivers 365 can route signals concurrently with the routing of data by transceivers coupled to different banks via the wafer-on-wafer bond 320. In various examples, the memory die can output data to the global IO lines 332 and the transceivers 365 concurrently. For example, control circuitry of the memory die can activate the LIOs 336 and the global IO lines 332 concurrently with the activation of the transceivers 365, by control circuitry of the logic die, to output signals to the logic die and to output signals through the traditional IO circuitry, which includes global IO lines 332.

In various instances, signals can be provided from a global bus of the memory die to the logic die. A transceiver of the logic die, coupled to the global bus, can be configured to route data from the memory die to the logic die. For example, the transceiver of the logic die can be activated to route signals from the global bus to the logic die. The transceivers configured to route signals from the global bus to the logic die can be different than the transceivers configured to route signals from the LIO lines 336 to the logic die. Two independent paths can be provided for routing signals from the memory die to the logic die. The first path can originate at the LIO lines 336. The second path can originate at the global bus of the memory die. The first path can be utilized by activating one or more transceivers of the logic die. The second path can be utilized by activating one or more different transceivers of the logic die. In various instances, the quantity of signals that can be routed concurrently from the LIO lines 336 to the logic die can be greater than the quantity of signals that can be routed concurrently from the global bus to the logic die.

FIG. 3G illustrates a portion of a tile in accordance with a number of embodiments of the present disclosure. The portion of the tile includes an LIO line 336 coupled to a transceiver 365 as compared to FIG. 3F in which the transceivers 365 are coupled to the sense amplifiers 363.

In FIG. 3G, the sense amplifiers 363 can output multiple signals. The signals can be output to the multiplexers 364. For example, the sense amplifiers 363-1, 363-2, ..., 363-N can output first signals to the multiplexer 364-1. The sense amplifiers 363-N+1, 363-N+2, ..., 363-M can output second signals to the multiplexer 364-2 while the sense amplifiers 363-M+1, 363-M+2, ..., 363-P can output signals to the multiplexer 364-S. Each of the multiplexers 364 can output signals to the LIOs 336.

The transceiver 365 can route the signals of the LIO lines 336 of the memory die to an LIO line 337 of the logic die, for example. In various examples, the memory die can activate the multiplexer 339 to output signals from the LIO lines 336 to the global IO lines 332 through a traditional IO circuitry of the memory device. The logic die can concurrently activate the transceiver 365 with the activation of the LIO lines 336 and the global IO lines 332 to output data to the logic die concurrent with outputting of the data via the IO circuitry of the memory die. For example, control circuitry of the memory device can determine whether to output data through the traditional IO circuitry of the memory device and control circuitry of the logic die can determine whether to output data to the logic die.

Although a single transceiver 365 is shown, multiple transceivers can be utilized to route signals from multiple LIO lines of a memory die to the logic die. For example, a transceiver can be coupled to an LIO line of a memory device of the memory die. Another transceiver can be coupled to an LIO line of another memory device of the memory die. Each of the transceivers can route signals to the logic die by routing the signals to LIO lines 337 of the logic die. Each of the transceivers can route signals concurrently. In various instances, the transceiver 365 can be coupled to the global IO line 332 instead of the sense amplifiers 363 or the LIO line 336. Similarly, the transceivers coupled to the global IO lines can concurrently route signals to the logic die.

Figure 4A:
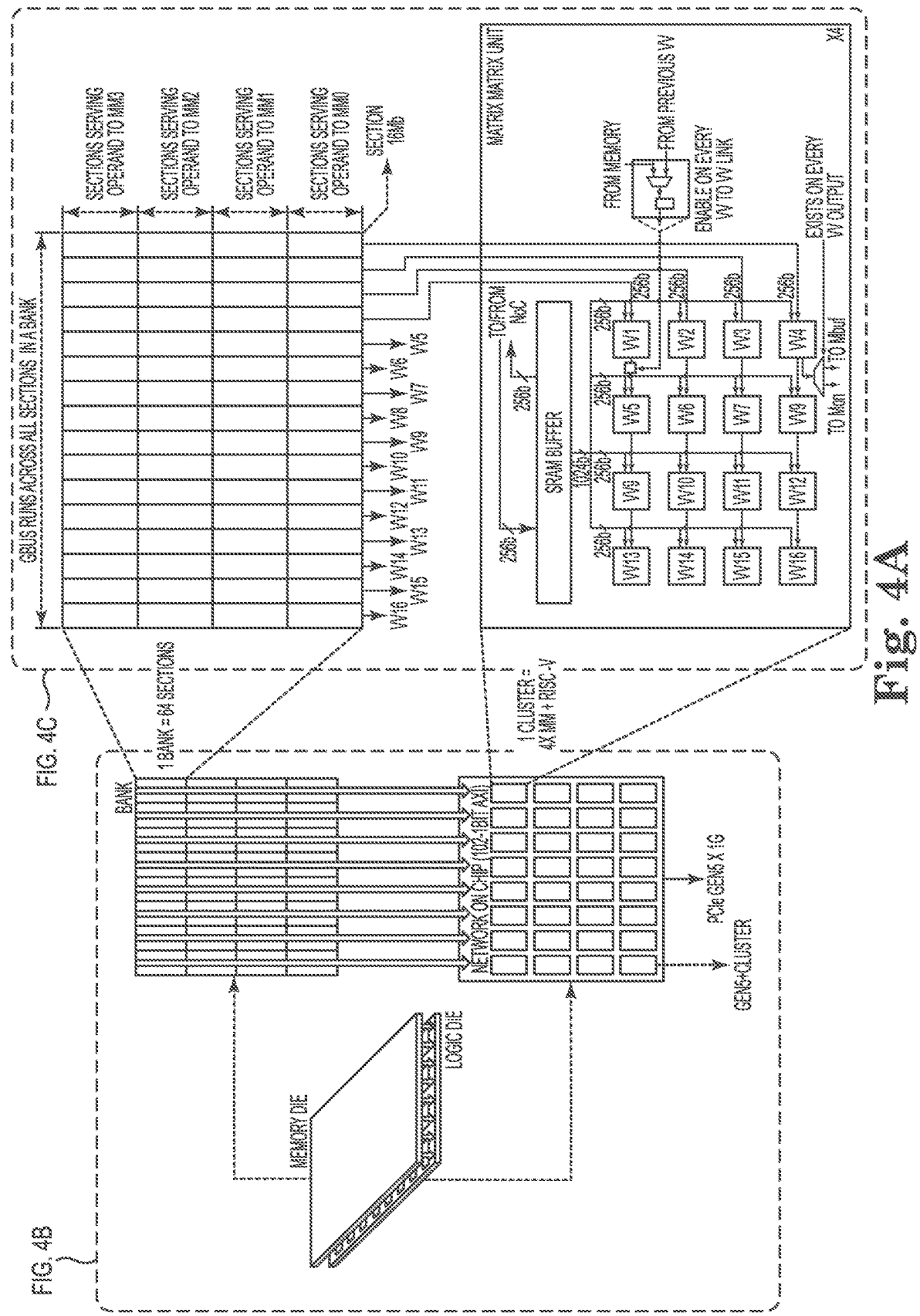
FIG. 4A is a block diagram of an example of a memory-logic architecture in accordance with a number of embodiments of the present disclosure.
Figure 4B:
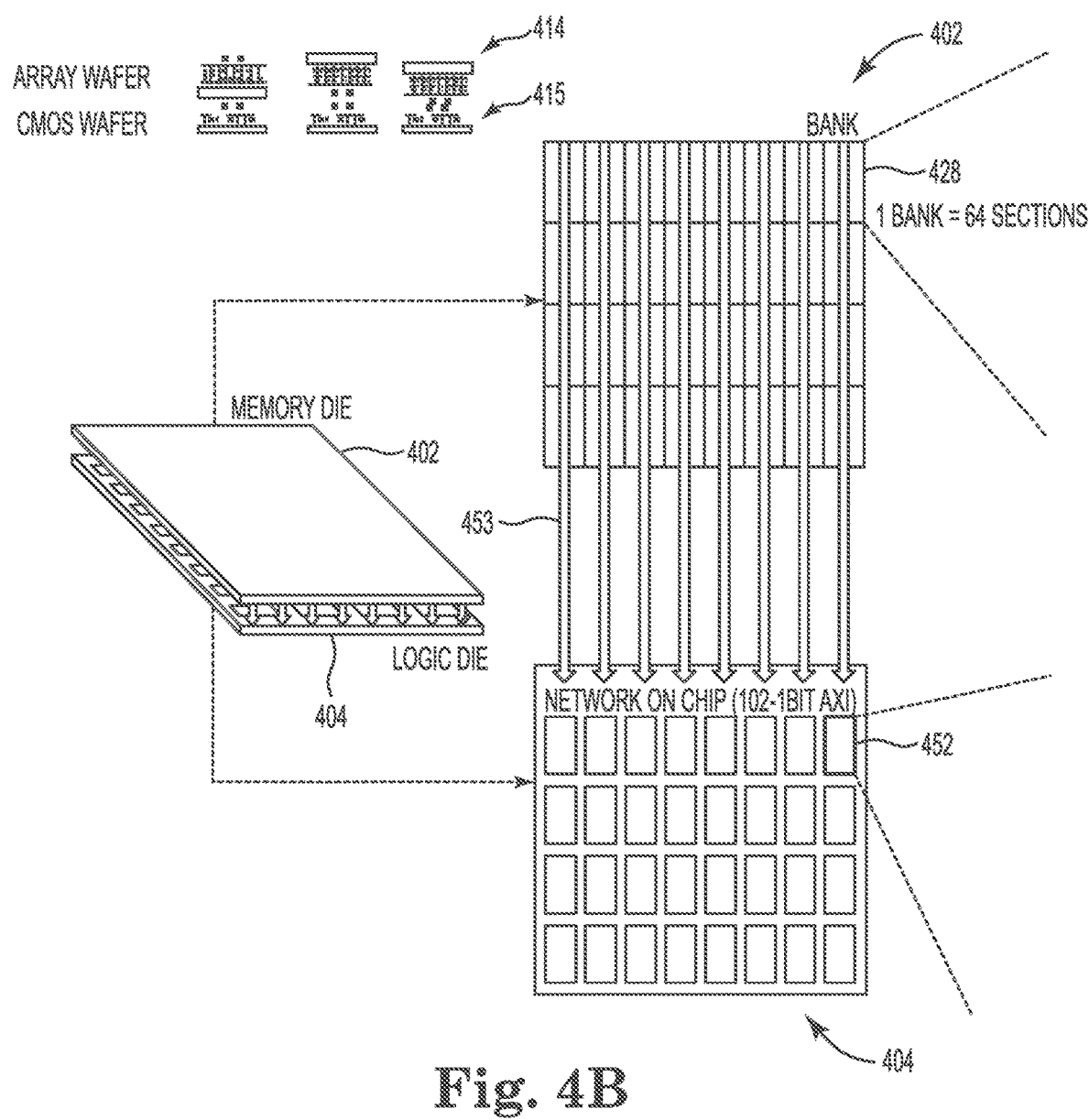
FIG. 4B is a block diagram of a first portion of the architecture illustrated in FIG. 4A.
Figure 4C:
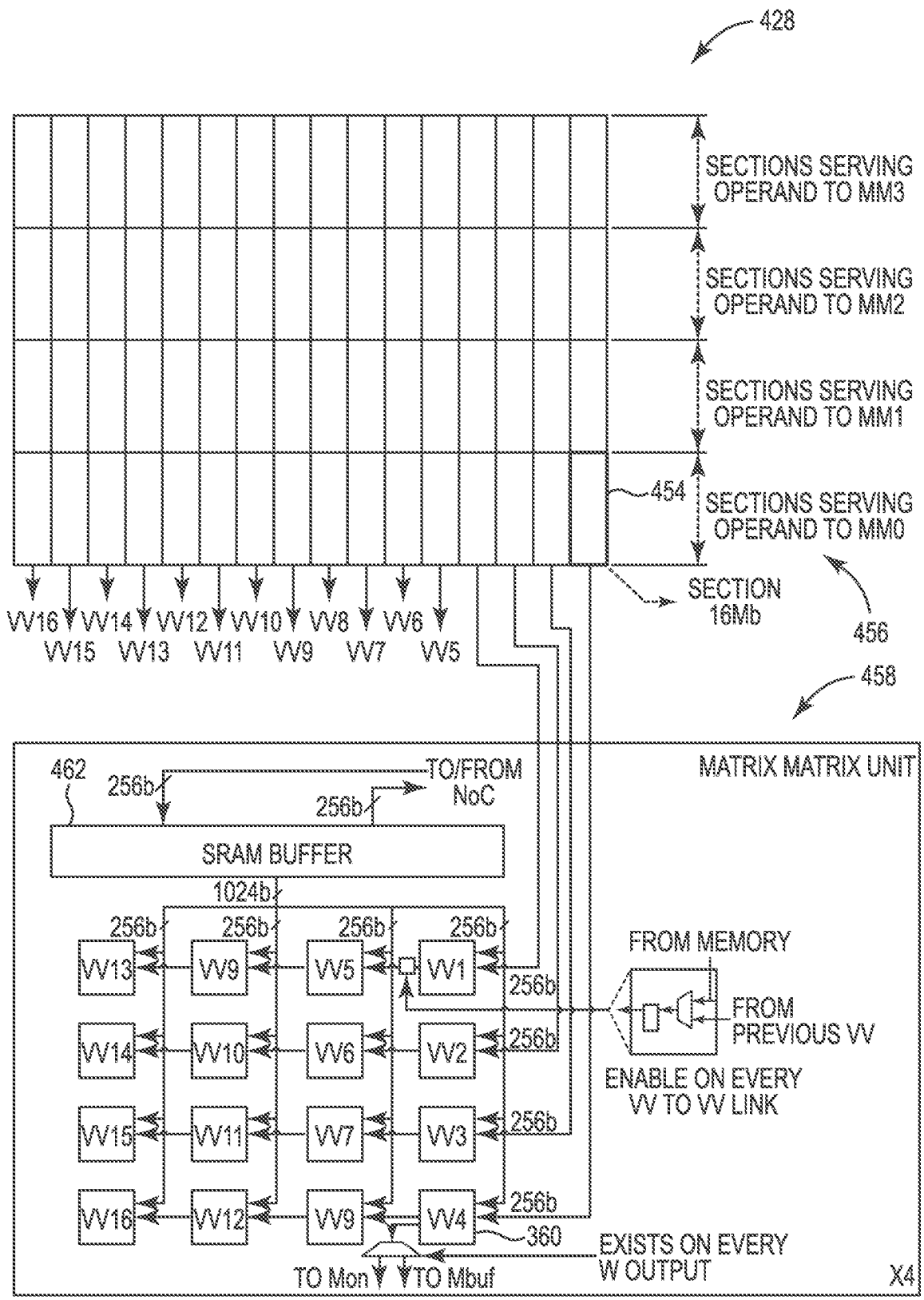
FIG. 4C is a block diagram of a second portion of the architecture illustrated in FIG. 4A.

FIG. 4A is a block diagram of an example of a memory-logic architecture in accordance with a number of embodiments of the present disclosure. FIG. 4B is a block diagram of a first portion of the architecture illustrated in FIG. 4A. FIG. 4C is a block diagram of a second portion of the architecture illustrated in FIG. 4A. The architecture includes a memory wafer 414 wafer-on-wafer bonded to a logic wafer 415. Singulated therefrom is a memory die 402 bonded to a logic die 404, in this example.

A portion of the memory die 402 is illustrated as a quantity of banks 428. In this example, there are 32 banks 428 per die 402 with a 1 gigabit per bank capacity for a total capacity for the die of 32 gigabits. Each bank 428 is divided (e.g., logically divided) into 64 sections 454, however, embodiments are not limited to this specific example. Each section has a capacity of 16 megabits. The sections 454 are arranged in rows 456.

A portion of the logic die 404 is illustrated as a quantity of clusters 452 forming a network-on-chip (e.g., a 1024 bit advanced extensible interface (AXI) network). In this example, the logic die 404 includes 32 clusters (corresponding to the 32 banks of the memory die 402). However, in some embodiments, the ratio of banks to clusters is other than 1:1. In this example, there are 1024 multiply accumulators (MACs) per cluster, operating at 1.2 gigahertz. Each cluster 452 is divided into 4 matrix-matrix units 458, however, embodiments are not limited to this specific example. One matrix-matrix unit 458 is illustrated as an example.

The memory die 402 is connected to the logic die 404 across 8 buses (GBUS) 453 in this non-limiting example. Each GBUS 453 is coupled to 4 banks 428 in a column and has a bus width of 256 bits across the 4 banks 428. The bandwidth of each GBUS 453 is 32 gigabytes per second for a full-chip bandwidth of 256 gigabytes per second. The memory capacity serviced by each GBUS 453 is 4 gigabits (1 gigabit per bank 428). Any data that is transferred to the logic die 404 is available to any of the resources of the logic die 404 via the network-on-chip architecture of the logic die 404.

Data can be exchanged between each of the four rows 456 of sections 454 of the memory bank 428 and a respective matrix-matrix unit 458. The matrix-matrix unit 458 can be included in logic circuitry of the logic die 404. In the example illustrated in FIG. 4C, the data from row 456 is provided to the matrix-matrix unit 458. The connection between each section 454 of a row 456 and the matrix-matrix unit 458 is a bus referred to as an LBUS. The width of the LBUS is 256 bits per section 454, servicing a 16 megabit memory space. The bandwidth is 32 gigabytes per second per LBUS, for a full-chip bandwidth between 4.5 and 65 terabytes per second. Each section 454 can exchange data with a respective vector-vector unit 460.

The matrix-matrix unit 458 includes 16 vector-vector units 460, which are coupled to an SRAM buffer 462 that is connected to the network-on-chip architecture of the logic die 404. Each vector-vector unit 460 is coupled to a respective memory section 454 and to one or more other vector-vector units 460. Each vector-vector unit 460 can be coupled to a respective LIO line of the memory device, to at least one other vector-vector unit 460, and to the buffer 462. The buffer 462 can be coupled to the GBUS 453, which can be coupled to a global IO line of the memory device. The logic circuitry can exchange signals indicative of data with the memory device via two different paths (the GBUS 453 and the LIO lines).

Figure 5:
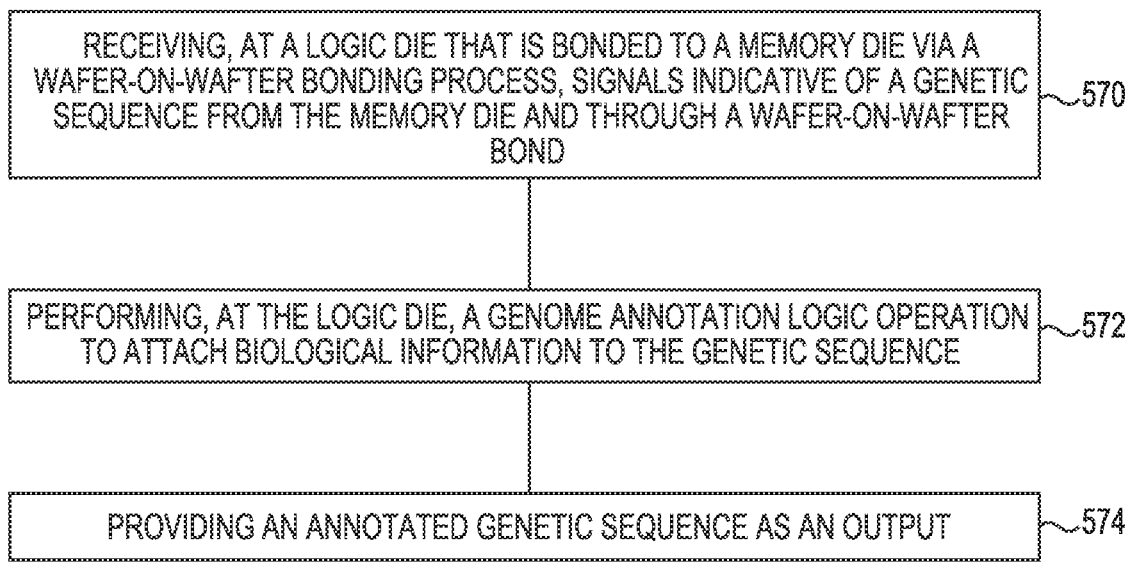
FIG. 5 is a flow diagram corresponding to a method for annotating a genomic sequence using a memory die and a logic die in accordance with a number of embodiments of the present disclosure.

FIG. 5 is a flow diagram corresponding to a method for annotating a genomic sequence using a memory die and a logic die in accordance with a number of embodiments of the present disclosure. Although shown in a particular sequence or order, unless otherwise specified, the order of the processes can be modified. Thus, illustrated embodiments should be understood only as examples, and the illustrated processes can be performed in a different order, and some processes can be performed in parallel. Additionally, one or more processes can be omitted in various embodiments. Thus, not all processes are required in every embodiment. Other process flows are possible.

At operation 570, signals indicative of a genetic sequence can be received at a logic die from a memory die that is bonded to the logic die via a wafer-on-wafer bonding process and through a wafer-on-wafer bond. For example, the logic die can receive the signals indicative of data representing the genetic sequence from the memory die and through the wafer-on-wafer bond using a bandwidth of 5 terabytes per second and using a power requirement of 8 watts. The genetic sequence can be a deoxyribonucleic acid (DNA) sequence, a ribonucleic acid (RNA) sequence, or another type of sequence.

At operation 572, a genome annotation logic operation can be performed at the logic die to attach biological information to the genetic sequence. The biological information attached to the genetic sequence can include introns, exons, intron-exon boundaries, regulatory sequences, repeats, gene names, open reading frames, untranslated regions, and protein products. In some embodiments, the logic die can perform the genome annotation logic operations on an amount of data that is greater than an amount of data transferred to a host as part of a single host memory access request. The method can also include predicting the protein products based on a given environmental condition. In some embodiments, the method can include differentiating multiple genes with an overlapping reading frame. The method can also include comparing the annotated genome sequence to a previously completed known annotated genome.

At operation 574, an annotated genetic sequence can be provided as an output. The method can include transmitting signals indicative of the annotated genetic sequence to a host via an output other than the wafer-on-wafer bond as part of providing the annotated genetic sequence. In some embodiments, the method can include generating a visual representation of the annotated genetic sequence and providing the visual representation of the annotated genetic sequence to a user via a user interface.

Figure 6:
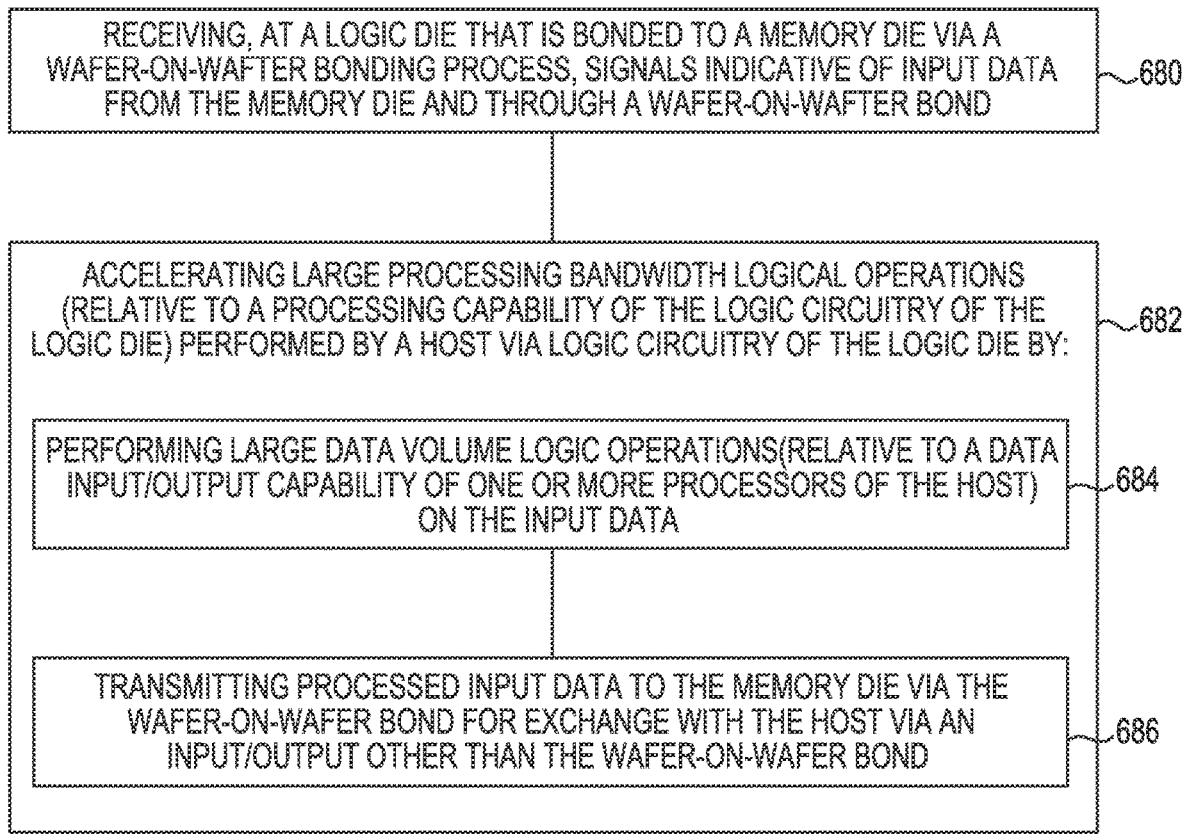
FIG. 6 is a flow diagram corresponding to a method for performing high data volume operations using a memory die and a logic die in accordance with a number of embodiments of the present disclosure.

FIG. 6 is a flow diagram corresponding to a method for performing high data volume operations using a memory die and a logic die in accordance with a number of embodiments of the present disclosure. At operation 680, signals indicative of input data can be received at a logic die from a memory die through a wafer-on-wafer bond. The memory die is bonded to the logic die via a wafer-on-wafer bonding process. In some embodiments, the input data can be received through the wafer-on-wafer bond from LIO lines of the memory die. At operation 682, large processing bandwidth logic operations performed by a host can be accelerated via logic circuitry of the logic die. At operation 684, the acceleration can be accomplished by performing large data volume operations on the input data. At operation 686, processed input data can be transmitted to the memory die via the wafer-on-wafer bond for exchange with the host via an input/output other than the wafer-on-wafer bond. The large processing bandwidth logic operations, performed at operation 682, are large relative to a processing capability of the logic circuitry of the logic die. The large data bandwidth logical operations performed at operation 684 are large relative to a data input/output capability of one or more processors of the host.

An example of the large processing bandwidth logical operations is fluid dynamic analysis operations. An example of the large data bandwidth operations is a description of a flow of fluids. The flow of fluids description can refer to an operation that provides a description of the movement of fluids under certain environmental conditions.

An example of the large processing bandwidth logical operations is graph analysis operations. An example of the large data bandwidth operations is node relationship operations. A node can be a data point representing any entity a user determines. For example, a node may be a commercial product, a customer, or particular services.

An example of the large processing bandwidth logical operations is natural language processing operations. An example of the large data bandwidth operations is speech recognition operations.

An example of the large processing bandwidth logical operations is image processing operations. An example of the large data bandwidth logical operations is image shading operations.

Other examples of the large data bandwidth logical operations include blockchain operations, facial recognition operations, augmented reality operations, and network traffic intrusion detection operations.

The specific quantities and connections illustrated herein are examples for explanatory purposes. One of ordinary skill in the art, having read and understood the present disclosure, could provide different quantities and arrangements of the specifically enumerated components.

As used herein, "a number of" something can refer to one or more of such things. For example, a number of memory devices can refer to one or more memory devices. A "plurality" of something means two or more.

Although specific embodiments have been illustrated and described herein, those of ordinary skill in the art will appreciate that an arrangement calculated to achieve the same results can be substituted for the specific embodiments shown. This disclosure is intended to cover adaptations or variations of various embodiments of the present disclosure. It is to be understood that the above description has been made in an illustrative fashion, and not a restrictive one. Combinations of the above embodiments, and other embodiments not specifically described herein will be apparent to those of skill in the art upon reviewing the above description. The scope of the various embodiments of the present disclosure includes other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method comprising:
   receiving, at a logic die that is bonded to a memory die via a wafer-on-wafter bonding process, signals indicative of a genetic sequence from the memory die and through a wafer-on-wafter bond;
   performing, at the logic die, a genome annotation logic operation to attach biological information to the genetic sequence; and
   providing an annotated genetic sequence as an output.

2. The method of claim 1, wherein providing the annotated genetic sequence comprises transmitting signals indicative of the annotated genetic sequence to a host via an output other than the wafer-on-wafer bond.

3. The method of claim 1, wherein the biological information attached to the genetic sequence includes introns, exons, intron-exon boundaries, regulatory sequences, repeats, gene names, open reading frames, untranslated regions, and protein products.

4. The method of claim 3, further comprising predicting the protein products based on a given environmental condition.

5. The method of claim 1, further comprising differentiating multiple genes with an overlapping reading frame.

6. The method of claim 1, further comprising comparing the annotated genome sequence to a previously completed known annotated genome.

7. The method of claim 1, further comprising:
generating a visual representation of the annotated genetic sequence; and
providing the visual representation of the annotated genetic sequence to a user via a user interface.

8. A method comprising:
receiving, at a logic die that is bonded to a memory die via a wafer-on-wafter bonding process, signals indicative of input data from the memory die and through a wafer-on-wafter bond; and
accelerating large processing bandwidth logical operations performed by a host via logic circuitry of the logic die by:
performing large data volume logic operations on the input data; and
transmitting processed input data to the memory die via the wafer-on-wafer bond for exchange with the host via an input/output other than the wafer-on-wafer bond;
wherein the large processing bandwidth logical operations are large relative to a processing capability of the logic circuitry of the logic die; and
wherein the large data bandwidth logical operations are large relative to a data input/output capability of one or more processors of the host.

9. The method of claim 8, wherein receiving the input data comprises receiving the input data through the wafer-on-wafer bond from a plurality of local input/output lines of the memory die.

10. The method of claim 8, wherein the large processing bandwidth logical operations comprise fluid dynamic analysis operations.

11. The method of claim 8, wherein the large processing bandwidth logical operations comprise graph analysis operations; and
wherein the large data bandwidth operations comprise node relationship operations.

12. The method of claim 8, wherein the large processing bandwidth logical operations comprise image processing operations; and
wherein the large data bandwidth logical operations comprise image shading operations.

13. The method of claim 8, wherein the large processing bandwidth logical operations comprise natural language processing operations.

14. The method of claim 8, wherein the large data bandwidth logical operations comprise blockchain operations.

15. The method of claim 8, wherein the large data bandwidth logical operations comprise facial recognition operations.

16. The method of claim 8, wherein the large data bandwidth logical operations comprise augmented reality operations.

17. The method of claim 8, wherein the large data bandwidth logical operations comprise network traffic intrusion detection operations.

18. An apparatus, comprising:
a memory die, comprising:
a memory array;
a plurality of local input/output lines (LIOs) coupled to the memory array; and
a global input/output line coupled to the plurality of LIOs and to a host interface;
a logic die bonded to the memory die via a wafer-on-wafer bonding process, the logic die comprising logic circuitry configured to:
receive signals indicative of data from the memory die and through a wafer-on-wafter bond to the plurality of LIOs, wherein the data comprises genetic sequence data;
perform genome annotation logic operations to attach biological information to the genetic sequence data; and
generate an annotated genetic sequence based on the genome annotation logic operations.

19. The apparatus of claim 18, wherein the logic circuitry is configured to perform the genome annotation logic operation on an amount of data that is greater than an amount of data transferred across the host interface as part of a single host memory access request.

20. The apparatus of claim 18, wherein the genetic sequence is a deoxyribonucleic acid (DNA) sequence or a ribonucleic acid (RNA) sequence.

* * * * *